US009389163B2

(12) United States Patent
Hedayat et al.

(10) Patent No.: US 9,389,163 B2
(45) Date of Patent: *Jul. 12, 2016

(54) SOOT SENSOR SYSTEM

(75) Inventors: Kayvan Hedayat, Weston, MA (US); John Hart, Lexington, OH (US); Eric Matson, Bellville, OH (US); Mark Wilson, Mansfield, OH (US); Norman Poirier, Raynham, MA (US)

(73) Assignee: Stoneridge, Inc., Warren, OH (US)

( * ) Notice: Subject to any disclaimer, the term of this patent is extended or adjusted under 35 U.S.C. 154(b) by 699 days.

This patent is subject to a terminal disclaimer.

(21) Appl. No.: 13/481,723

(22) Filed: May 25, 2012

(65) Prior Publication Data

US 2012/0324981 A1  Dec. 27, 2012

Related U.S. Application Data

(60) Provisional application No. 61/490,310, filed on May 26, 2011.

(51) Int. Cl.
*G01N 15/06* (2006.01)
*F01N 11/00* (2006.01)
*G01N 15/00* (2006.01)

(52) U.S. Cl.
CPC ........ *G01N 15/0656* (2013.01); *G01N 15/0606* (2013.01); *F01N 2560/05* (2013.01); *G01N 2015/0046* (2013.01)

(58) Field of Classification Search
CPC .................. G01N 15/0656; F01N 2560/05
USPC ........... 73/23.31, 23.33, 28.01; 204/424, 426, 204/428, 429; 422/82.01, 82.02
See application file for complete search history.

(56) References Cited

U.S. PATENT DOCUMENTS

| 4,300,990 | A | 11/1981 | Maurer |
| 4,383,158 | A | 5/1983 | Niwa |
| 4,523,086 | A | 6/1985 | Eilentropp |
| 4,567,750 | A | 2/1986 | Artmann |
| 4,656,832 | A | 4/1987 | Yukihisa et al. |
| 6,377,052 | B1 | 4/2002 | McGinnis et al. |
| 6,634,210 | B1 | 10/2003 | Bosch et al. |

(Continued)

FOREIGN PATENT DOCUMENTS

| CN | 101163962 A | 4/2008 |
| DE | 102006046837 | 4/2008 |

(Continued)

OTHER PUBLICATIONS

International Search Report and Written Opinion mailed Sep. 6, 2012 in corresponding PCT Patent Application No. PCT/US12/039757.

(Continued)

*Primary Examiner* — Laura Martin
*Assistant Examiner* — Rose M Miller
(74) *Attorney, Agent, or Firm* — Grossman, Tucker, Perreault & Pfleger, PLLC

(57) ABSTRACT

A soot sensor includes a soot sensor including a first element on a first surface of the soot sensor. A soot sensing system may include a soot sensor and circuitry electrically coupled to the first element of the soot sensor. The circuitry is configured to determine an amount of soot accumulated on the first element and to control heating of the first element in response to the soot accumulation.

17 Claims, 34 Drawing Sheets

(56) References Cited

U.S. PATENT DOCUMENTS

| | | |
|---|---|---|
| 6,794,981 B2 | 9/2004 | Padmanabhan et al. |
| 7,543,477 B2 | 6/2009 | Berger et al. |
| 7,574,895 B2 | 8/2009 | Schnell et al. |
| 8,035,404 B2 | 10/2011 | Schnell et al. |
| 2002/0186007 A1* | 12/2002 | Cao et al. ............... 324/207.16 |
| 2003/0154764 A1* | 8/2003 | Stahl et al. ................... 73/23.2 |
| 2003/0196499 A1 | 10/2003 | Bosch et al. |
| 2005/0275497 A1* | 12/2005 | Ramadan et al. ............ 336/200 |
| 2007/0258186 A1* | 11/2007 | Matyushkin et al. ......... 361/234 |
| 2008/0190173 A1* | 8/2008 | Wienand et al. ............ 73/28.01 |
| 2008/0295575 A1* | 12/2008 | Tokuyasu et al. ........... 73/23.31 |
| 2009/0019918 A1 | 1/2009 | Baars et al. |
| 2009/0090622 A1 | 4/2009 | Ripley |
| 2009/0139081 A1 | 6/2009 | Nelson |
| 2009/0217737 A1 | 9/2009 | Dorfmueller et al. |
| 2010/0095657 A1 | 4/2010 | Gonze et al. |
| 2010/0147052 A1 | 6/2010 | Nelson et al. |
| 2010/0180669 A1 | 7/2010 | Baars et al. |

FOREIGN PATENT DOCUMENTS

| | | |
|---|---|---|
| GB | 2029028 | 3/1980 |
| JP | 59-196453 | 11/1984 |
| JP | 59197847 A | 11/1984 |
| JP | 61186846 | 8/1986 |
| JP | 61186846 A | 8/1986 |
| JP | S62-018655 | 2/1987 |
| JP | 2009085959 A | 4/2009 |
| JP | 2010-078429 | 4/2010 |
| WO | 9926053 | 5/1999 |

OTHER PUBLICATIONS

Chinese Office Action issued Nov. 15, 2014 in corresponding Chinese Patent Application No. 201280031796.6.
European Search Report issued Nov. 21, 2014 in corresponding European Patent Application No. 12789260.2.
Japanese Office Action issued Feb. 29, 2016 in corresponding Japanese Application Serial No. 2014-512177.

* cited by examiner

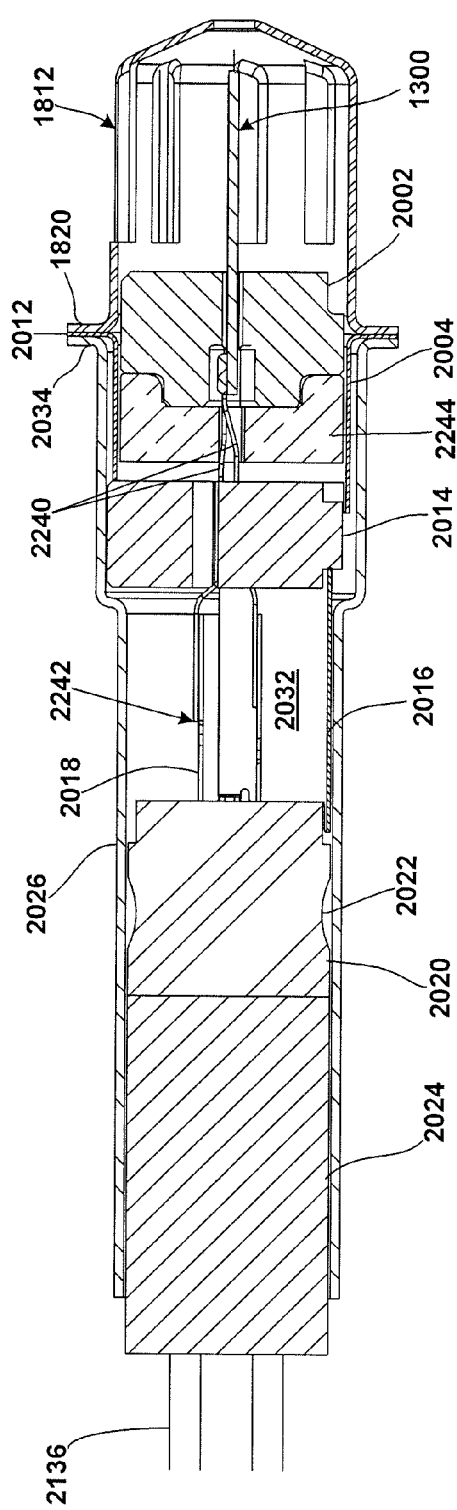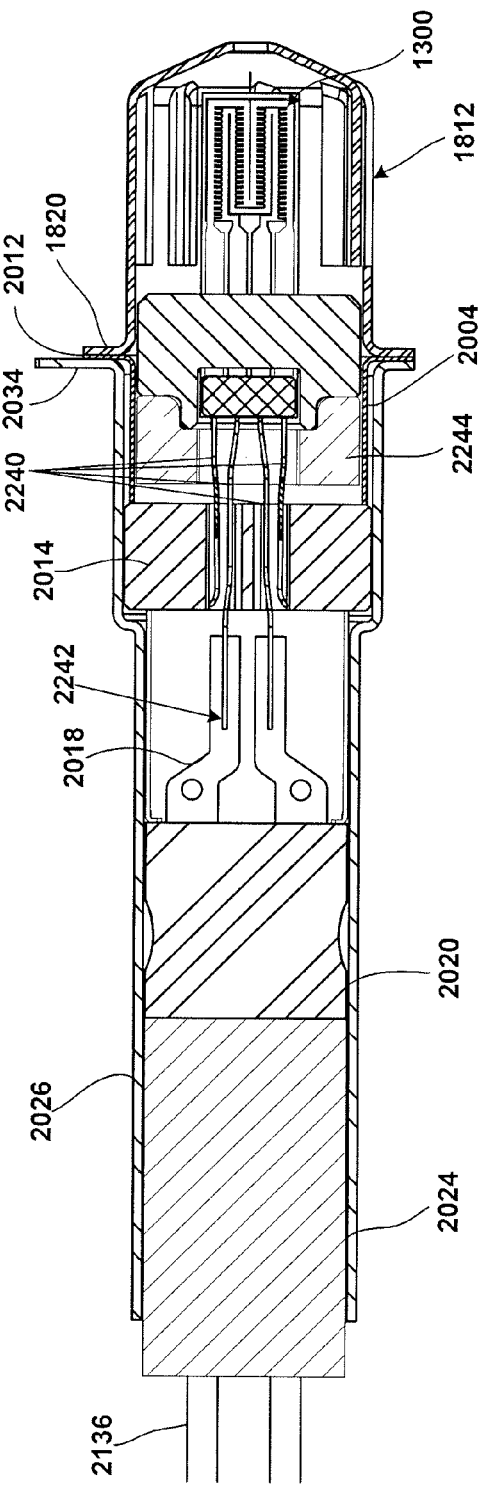
FIG. 22A
FIG. 22B

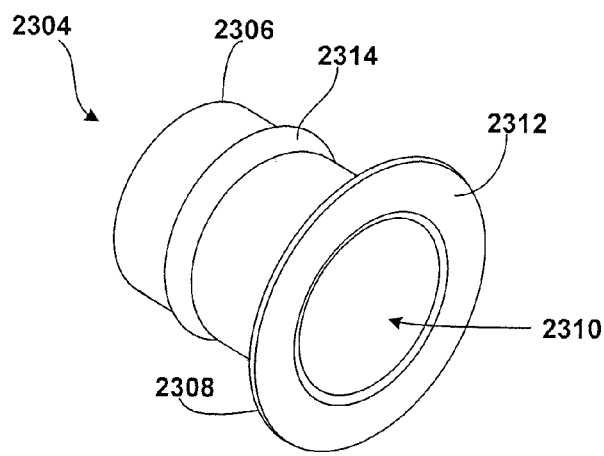
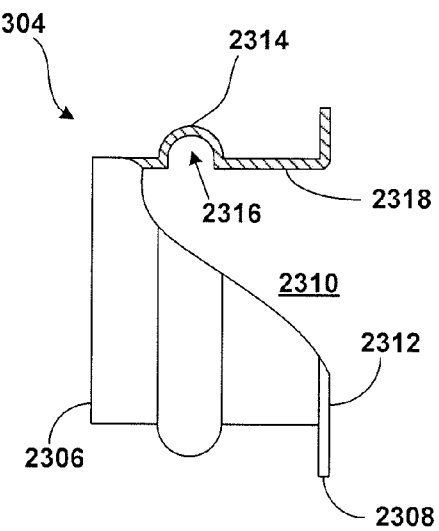
FIG. 23A  FIG. 23B
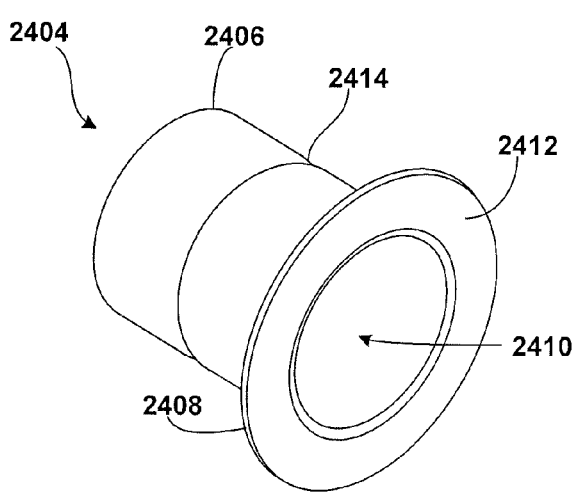
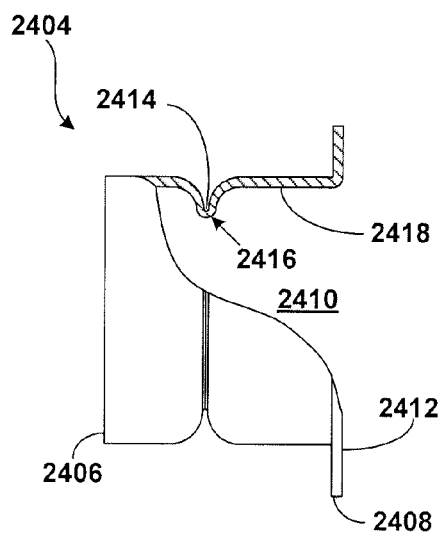
FIG. 24A  FIG. 24B

SOOT SENSOR SYSTEM

CROSS REFERENCE TO RELATED APPLICATIONS

The present application claims the benefit of U.S. Provisional Patent Application Ser. No. 61/490,310, filed May 26, 2011, the entire disclosure of which is incorporated herein by reference.

FIELD

The present disclosure relates generally to a soot sensor, and, more particularly, to a sensor system for detecting soot in an exhaust gas flow.

BACKGROUND

Soot sensors may be used in engine emissions applications, e.g. for on-board diagnostics (OBD). A sensor of this type may be used to detect and measure particulate matter build-up, e.g. soot concentration, in an engine exhaust gas. In diesel engines in particular, it is desirable to have the lowest possible soot particle concentration when exhaust gas is released into the environment. To monitor the operating status of the internal combustion engine, it is expedient for this purpose to position a soot sensor in the exhaust system associated with the internal combustion engine. The soot sensor may be positioned upstream or downstream from a diesel particulate filter (DPF). If it is positioned downstream from the DPF, function monitoring of the DPF may also be performed using the soot sensor. When the DPF fails, the soot sensor may detect excessive soot in engine exhaust and alert the vehicle engine control unit (ECU).

Soot sensors may be relatively simple resistive devices. FIG. 1 is a schematic top view of one known configuration of a soot sensor having an on-board heater element, and FIG. 2 is a schematic bottom view of the soot sensor of FIG. 1. The sensor 100 may include a non-conductive substrate 102 defining a first surface 104 and a second surface 106 opposite the first surface 104. A sense element 108 is formed on the first surface 104 of the substrate 102, and includes a conductive material defining a first electrode 110 and a separate second electrode 112. The conductive material may be a precious metal selected to withstand high temperatures, and the first 110 and second 112 electrodes may be electrically separate from each other to establish an open circuit therebetween.

As shown, the first and second electrodes 110, 112 may be configured with inter-digitized "fingers" that maximize a perimeter between the first and second electrodes 110, 112. The first electrode 110 defines a first set of fingers 114 and the second electrode 112 defines a separate second set of fingers 116. In operation, when soot (not shown) from exhaust lands on the sensing element 108, carbon in the soot electrically connects the first and second electrodes 110, 112, effectively lowering the resistance therebetween. The resistance between the electrodes is measured as an indication of the amount of soot present.

FIG. 3 is an enlarged sectional view of the soot sensor of FIGS. 1 and 2 taken along line 3-3. As shown in FIGS. 2 and 3, in some applications, the sensor 100 will also have an on-board heater element 118 implemented on the second surface 106 of the substrate 102. The on-board heater element 118 is configured to heat the soot sensor 100 through resistive heating. For example, it may be desirable to clean off soot that has collected on the first and/or second surfaces 104, 106 of the substrate 102. The on-board heater element 118, which may include a platinum trace with a known resistance, may be activated, heating the sensor element 108 to a relatively high temperature, e.g. 650° C., thereby causing any accumulated soot particles to incinerate.

A soot sensor of the type described above is susceptible to breakdown under the conditions existing in the exhaust system. The electrodes are directly subjected to exhaust gas flow, wherein certain exhaust materials may lead to corrosion of the electrodes and/or contamination of the sensor surface, which may have an interfering effect on soot accumulation measurement. Additionally, the sense element of current soot sensors lacks diagnostic functions capable of sensing a break in the sense element traces. Moreover, on-board heaters included in current soot sensors have difficulty reaching high temperatures required to sufficiently incinerate accumulated soot during high flow conditions.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIG. 22A is a sectional view of the soot sensor assembly of FIG. 21 taken along lines A-A;

FIG. 22B is a section view of the soot sensor assembly of FIG. 21 taken along lines B-B;

FIGS. 23A-23B are perspective and sectional views of one embodiment of a portion of the soot sensor assembly of FIG. 20;

FIGS. 24A-24B are perspective and sectional views of another embodiment of a portion of the soot sensor assembly of FIG. 20;

DETAILED DESCRIPTION

The present disclosure is generally directed to soot sensors and a soot sensor system for detecting soot particles. In general, a soot sensor system consistent with the present disclosure includes a substrate defining a first surface and a second surface opposing the first surface. At least one element having at least one continuous loop of conductive material is disposed on the first surface of the substrate. The at least one element is configured to operate in a first mode to sense accumulation of soot on at least said first surface of said substrate and to operate in a second mode to remove accumulated soot on at least said first surface of said substrate. First and second electrical contacts are disposed at opposite ends of the at least one element. Circuitry is electrically coupled to the first and second electrical contacts and configured to determine an amount of soot accumulated on the first surface of the substrate and the element and to control heating of the element in response to soot accumulation.

A soot sensor and/or soot sensor system consistent with the present disclosure may be configured to be positioned in an exhaust system of a motor vehicle having a diesel engine. Additionally, a soot sensor and/or soot sensor system may be configured for use in the field of household technology in an oil heating system, for example, it being provided with an appropriately designed support depending on the application. For use in an exhaust system of a motor vehicle, a soot sensor system consistent with the present disclosure may be configured to detect soot accumulation from exhaust gas flow. Additionally, the soot sensor system may be coupled to and configured to communicate with an onboard diagnostics system of a vehicle. Additionally, the soot sensor may be positioned downstream from a diesel particulate filter (DPF) of a motor vehicle having a diesel engine, wherein the sensor may be configured to monitor the performance of the DPF.

Figure 1:
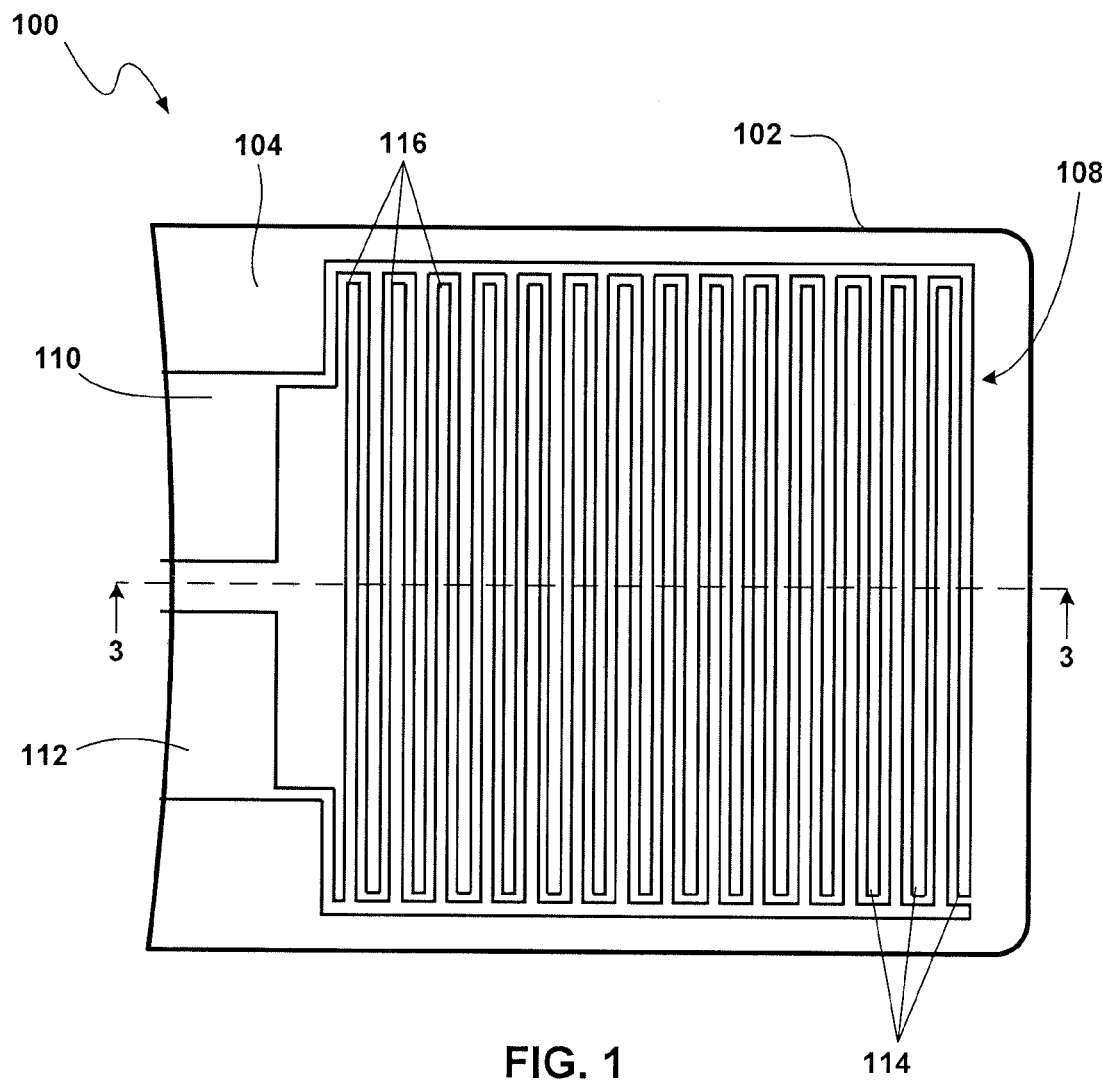
FIG. 1 is a schematic top view of a soot sensor.
Figure 2:
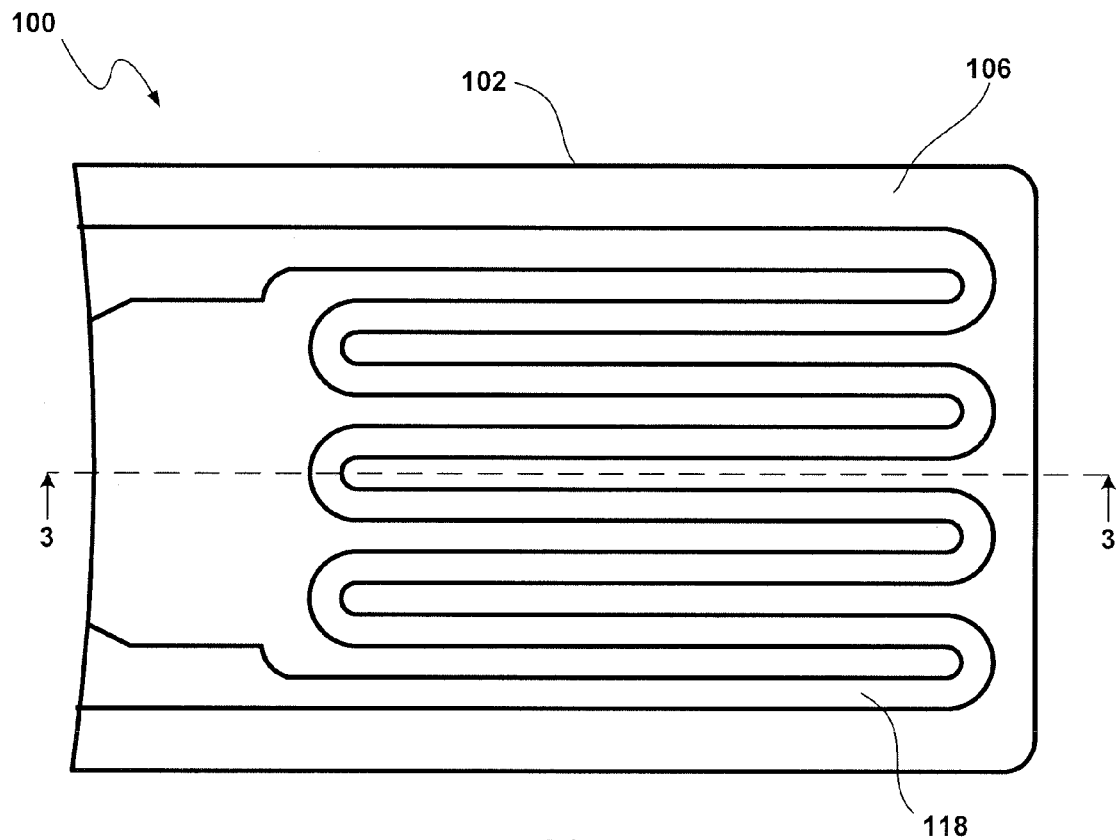
FIG. 2 is a schematic bottom view of the soot sensor of FIG. 1.
Figure 3:
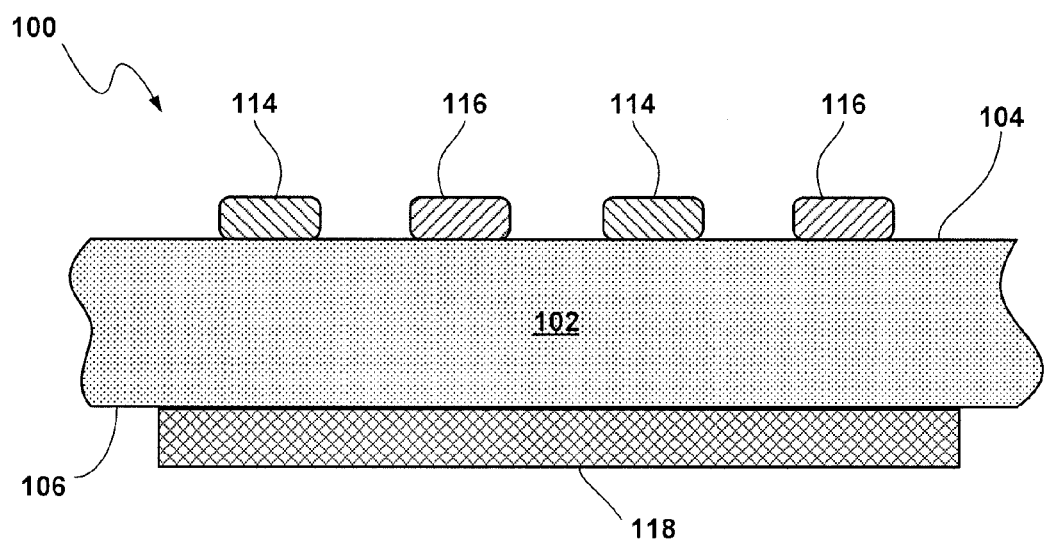
FIG. 3 is an enlarged sectional view of the soot sensor of FIGS. 1 and 2 taken along line 3-3.
Figure 4:
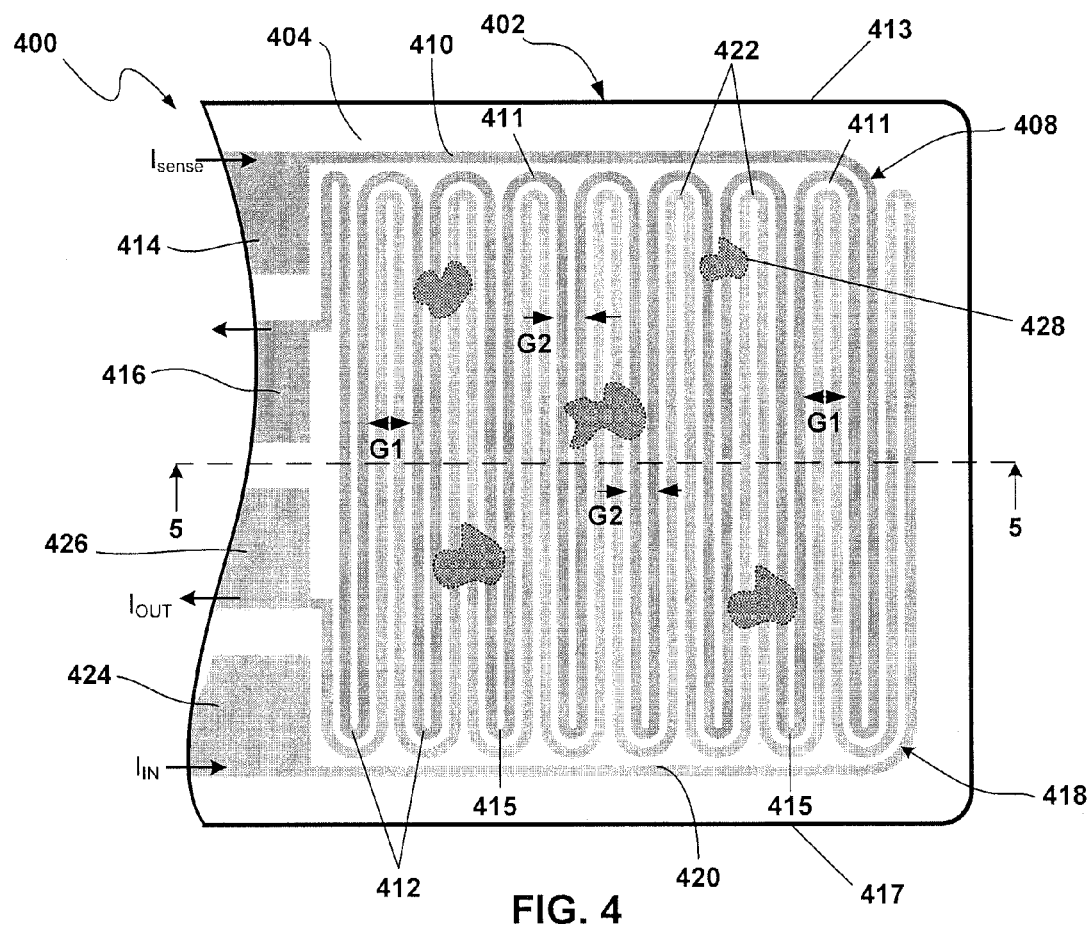
FIG. 4 is a schematic top view of a soot sensor consistent with the present disclosure.
Figure 5A:
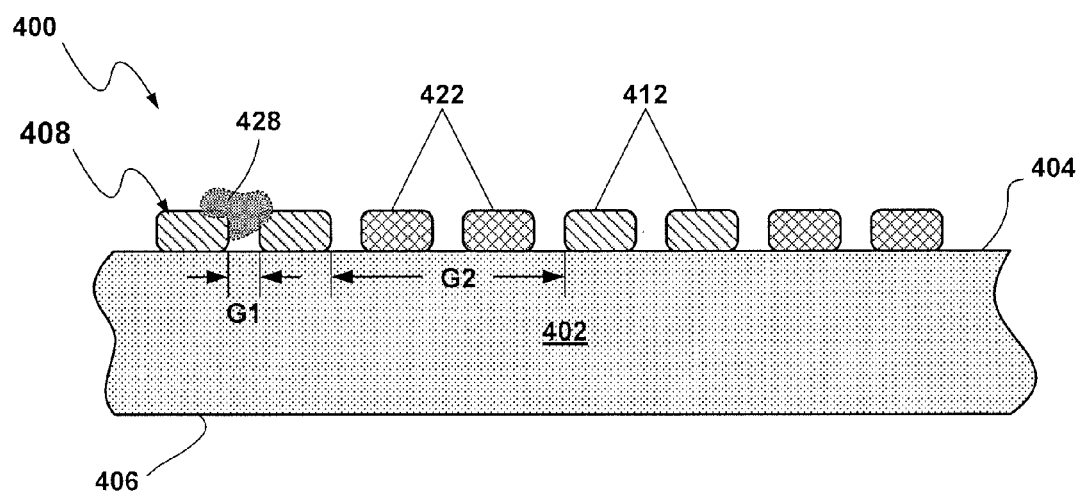
FIG. 5A is a sectional view of a portion of the soot sensor of FIG. 4 taken along line 5-5 consistent with the present disclosure.

Referring to FIG. 4, an embodiment of a soot sensor consistent with the present disclosure is schematically depicted. The soot sensor 400 includes a substrate 402, e.g. constructed from a dielectric or non-conductive material, defining a first surface 404 (e.g. a top surface, as shown in FIG. 5A) and a second surface 406 (e.g. a bottom surface, as shown in FIG. 5A) opposing the first surface 404. The soot sensor 400 includes a sensor element 408 formed on the first surface 404 of the substrate 402. The sensor element 408 includes at least one continuous loop 410 of conductive material disposed on the substrate 402. The loop 410 may take any regular and/or irregular geometric shape, e.g. serpentine, spiral, rectangular, circular, etc.

In the illustrated exemplary embodiment, the loop 410 is arranged in a serpentine configuration including a first set of a plurality of undulations 412 and a plurality of gaps G1 and G2 defined within and between each of the plurality of undulations 412. In the illustrated embodiment, the portions of the loop 410 including turns 411 adjacent the side 413 of the sensor are separated by gaps G1 and the portions of the loop 410 including turns 415 adjacent the side 417 of the sensor are separated by gaps G2, and the gaps G1 are wider than the gaps G2. The term "serpentine" as used herein refers to a configuration including turns of any shape, e.g. arcuate as show in FIG. 4, square, combinations of arcuate and square etc. and also includes turns separated by gaps of uniform and/or differing sizes.

The sensor element 408 further includes first and second electrical contacts 414, 416 at opposite ends of the loop 410. The first and second electrical contacts 414, 416 may be configured for coupling to circuitry for providing current through the loop 410. In the illustrated embodiment, an input current $I_{sense}$ may be provided at the first electrical contact 414 (or second electrical 416 contact).

The value of $I_{sense}$ may be representative of the amount of soot disposed on the sensor 400. In the illustrated embodiment, for example, soot particles 428 are shown as accumulated on the first surface 404 of the substrate 402, including on the sensor element 408. As soot 428 builds up on the sensor element, the resistance of the loop 410 changes, which changes the value of $I_{sense}$. The value of $I_{sense}$ is thus representative of the amount of soot accumulated on the sensor.

The sensor element 400 further include a heater element 418 formed on the first surface 404 of the substrate 402. The heater element 418 includes at least one continuous loop 420 of conductive material disposed on the substrate 402. The loop 420 may take any regular and/or irregular geometric shape, e.g. serpentine, spiral, rectangular, circular, etc, and may be positioned adjacent the sensor element loop 410 in at least a portion of its length.

In the illustrated exemplary embodiment, the loop 420 is arranged in a serpentine configuration including a second set of a plurality of undulations 422 complementary to and interweaving with the first set of plurality of undulations 412. The heater element 418 further includes first and second electrical contacts 424, 426 at opposite ends of the loop 420. The first and second electrical contacts 424, 426 may be configured for coupling to circuitry for providing current through the loop 420. In the illustrated embodiment, an input current $I_{heater}$ may be provided at the first electrical contact 424 (or second electrical 426 contact). In one embodiment, for example, when a threshold amount of soot 428 accumulates on the sensor element 408, e.g. as determined by reaching a threshold value of $I_{sense}$, the heater current $I_{heater}$ may be applied to cause the heater element 418 to heat and at least partially remove, e.g. incinerate, the soot 428, thereby cleaning/regenerating the sensor 400 for continued use.

The sensor element 408 may include electrically conductive materials or metals, such as, gold, platinum, osmium, rhodium, iridium, ruthenium, aluminum, titanium, zirconium, and the like, as well as, oxides, alloys, and combinations including at least one of the foregoing metals. The heater element 418 may include various materials. For example, materials may include platinum, gold, palladium, and the like and/or alloys, oxides, and combinations thereof. The substrate 402 may include a non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and providing structural integrity and/or physical protection. Additionally, the soot sensor 400 may include thick film and/or thin film constructions.

FIG. 5A is a sectional view of a portion of the soot sensor 400 of FIG. 4 taken along line 5-5 consistent with one embodiment of the present disclosure. In the illustrated embodiment, soot particles 428 are accumulated on at least the sensor element 408. In particular, when exposed to exhaust gas flow, the soot particles 428 may accumulate within at least one of the plurality of gaps G1 and/or G2 defined within and between each of the plurality of undulations 412 of the loop 410 of the sensor element 408. When the sensor element 408 is free of any soot particles, the electrical circuit of the sensor element 408 created between the first and second electrical contacts 414, 416 has a first resistance. When soot particles 428 accumulate on the sensor element 408, and, in particular, within at least one of the plurality of gaps G1 and/or G2, wherein the soot particle 428 makes contact with the loop 410, the resistance between the first and second electrical contacts 414, 416 may change. Resistance may increase as more soot particles 428 collect and accumulate. The heater element 418 may be activated when it is desired to have accumulated soot particles 428 removed from the soot sensor 408. The heater element 418 may be configured to reach a temperature at which soot particles 428 are incinerated.

Figure 5B:
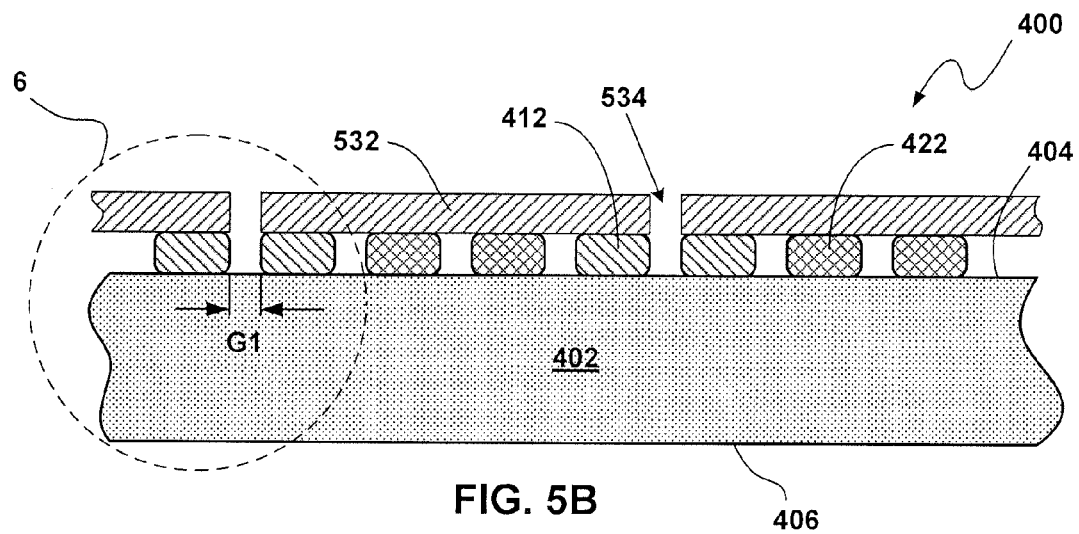
FIG. 5B is a sectional view of a portion of the soot sensor of FIG. 4 taken along line 5-5 according to another embodiment consistent with the present disclosure.
Figure 6:
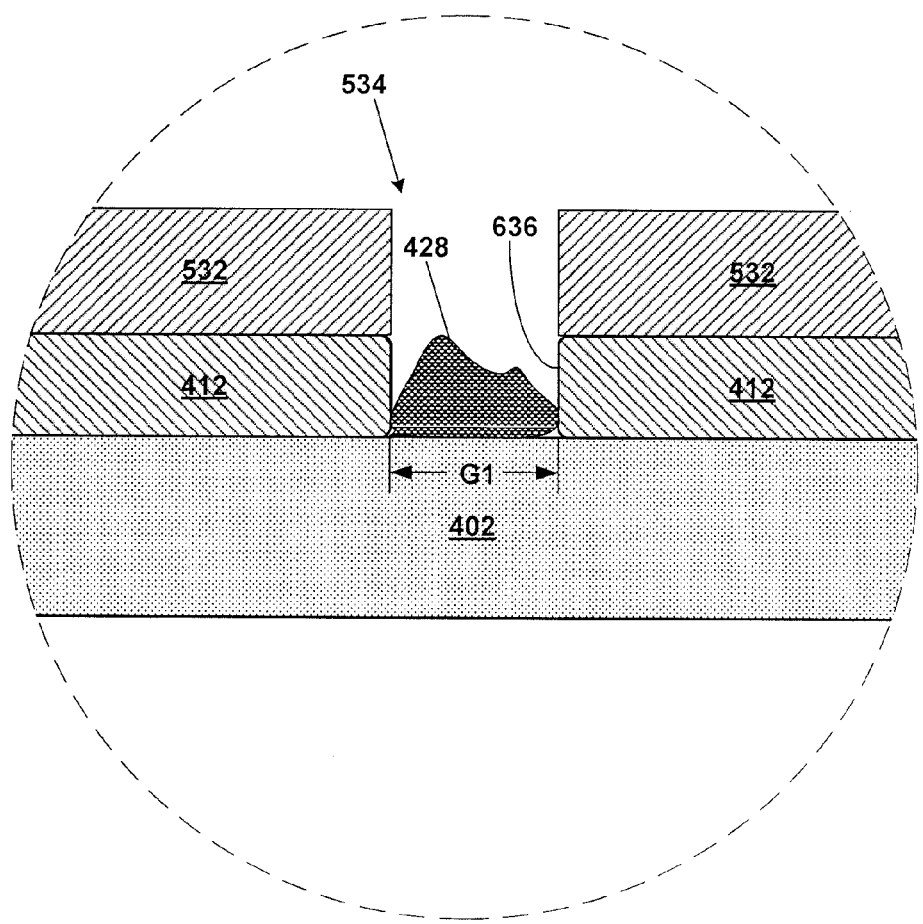
FIG. 6 is an enlarged view of the portion of the soot sensor of FIG. 5B.

FIG. 5B is a sectional view of a portion of the soot sensor of FIG. 4 taken along line 5-5 according to another embodiment consistent with the present disclosure and FIG. 6 is an enlarged view of a portion of the soot sensor of FIG. 5B. In one embodiment, a protective layer 532 is formed over the first surface 404 of the substrate 402 and covers at least a portion of the undulations 412, 422 of the sensor and heater elements 408, 418, respectively. The protective layer 532 may be configured to insulate at least a portion of the undulations 412 of the sensor element 408 from exhaust gas flow. The protective layer 532 further defines a plurality of channels 534 corresponding to and aligned with the plurality of gaps G1 defined by the undulations 412 of sensor element 408.

Referring to FIG. 6, each of the plurality of channels 534 exposes at least a portion of the sensor element, e.g. edges 636 of the undulations 412, to exhaust gas flow and the soot particles 428. In the illustrated embodiment, each of the plurality of channels 534 are sized and/or shaped to allow soot particles 428 to accumulate within at least one of the plurality of channels 534 and the corresponding gap G1, such that soot particles 428 make contact with at least a portion of the exposed sensor element 408 conductive material, e.g. edges 636 of the undulations 412.

Figure 7:
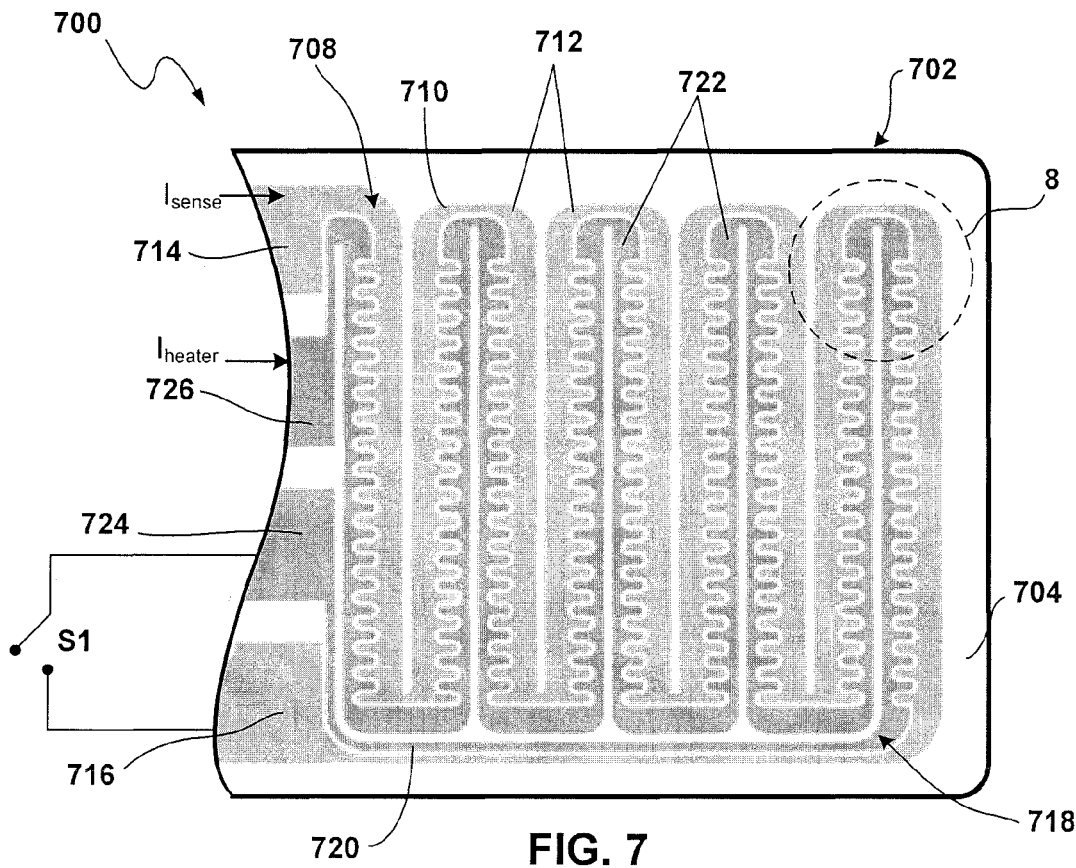
FIG. 7 is a schematic top view of another embodiment of a soot sensor consistent with the present disclosure.
Figure 8A:
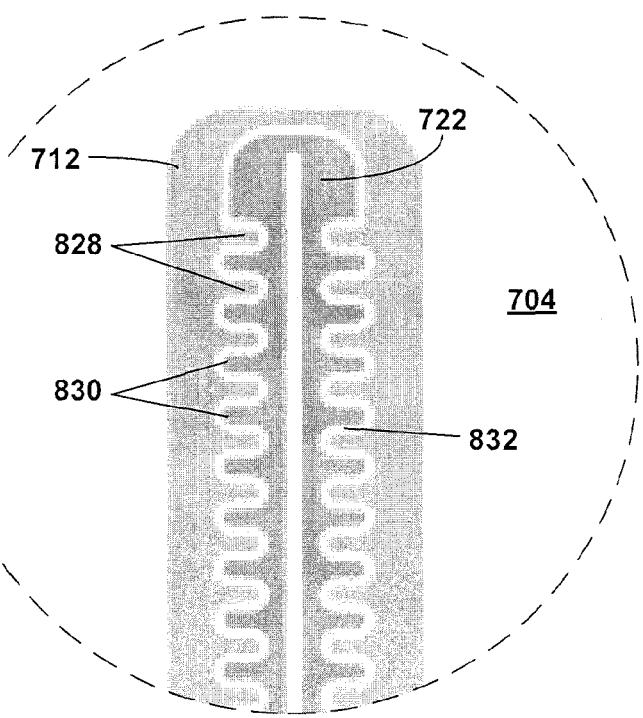
FIG. 8A is an enlarged view of a portion of the soot sensor of FIG. 7.

FIG. 7 is a schematic top view of another embodiment of a soot sensor consistent with the present disclosure and FIG. 8A is an enlarged view of a portion of the soot sensor of FIG. 7. This embodiment is similar to the embodiment of FIG. 4, and like components have been assigned like reference numerals in the seven hundreds rather than the four hundreds. The soot sensor 700 includes a substrate 702 defining a first surface 704. A sensor element 708 and a heater element 718 are formed on the first surface 704. The sensor and heater elements 708, 718 each include at least one continuous loop of conductive material 710, 720, respectively, disposed on the substrate 702. Similar to the embodiment of FIG. 4, the loops 710, 720 may be arranged in a serpentine configuration including first 712 and second 722 sets of undulations. Referring to FIG. 8A, the first 712 and second 722 sets undulations further define first 828 and second 830 subsets of undulations, respectively. A plurality of gaps 832 are defined within and between each of the first 828 and second 830 subsets of plurality of undulations.

The sensor element 708 further includes first 714 and second 716 electrical contacts at opposite ends of the loop 710. The first and second electrical contacts 714, 716 may be configured for coupling to circuitry for providing current through the loop 710. In the illustrated embodiment, an input current $I_{sense}$ may be provided at the first electrical contact 714 (or second electrical 716 contact). Similarly, the heater element 718 further includes first 724 and second 726 electrical contacts at opposite ends of the loop 720. The first and second electrical contacts 724, 726 may be configured for coupling to circuitry for providing current through the loop 720. In the illustrated embodiment, an input current $I_{heater}$ may be provided at the first electrical contact 724 (or second electrical 726 contact).

In the illustrated embodiment, the sensor and heater elements 708, 718 may be configured to be operated separately and independently from one another as described above regarding the embodiment of FIG. 4. Additionally, the soot sensor 700 may further include a switch S1 coupled to the first 724 and second 716 electrical contacts of the heater 718 and sensor 708 elements, respectively, for selectively coupling and decoupling the contacts 724, 716. When the switch S1 is open, the sense current $I_{sense}$ is determined by the resistance of the associated with the loop 710 of conductive material between contacts 714 and 716 and varies with soot particles deposited on the loop 710, thereby allowing the sensor element to sense soot particles. When the switch S1 is closed, loops 710 and 720 are electrically coupled in series establishing a single continuous loop of conductive material between the contacts 714 and 726. The current $I_{sense}$ may then pass through both the sensor 708 and heater 718 elements to allow both the sensor 708 and heater 718 elements to act as a single heater element.

Figure 8B:
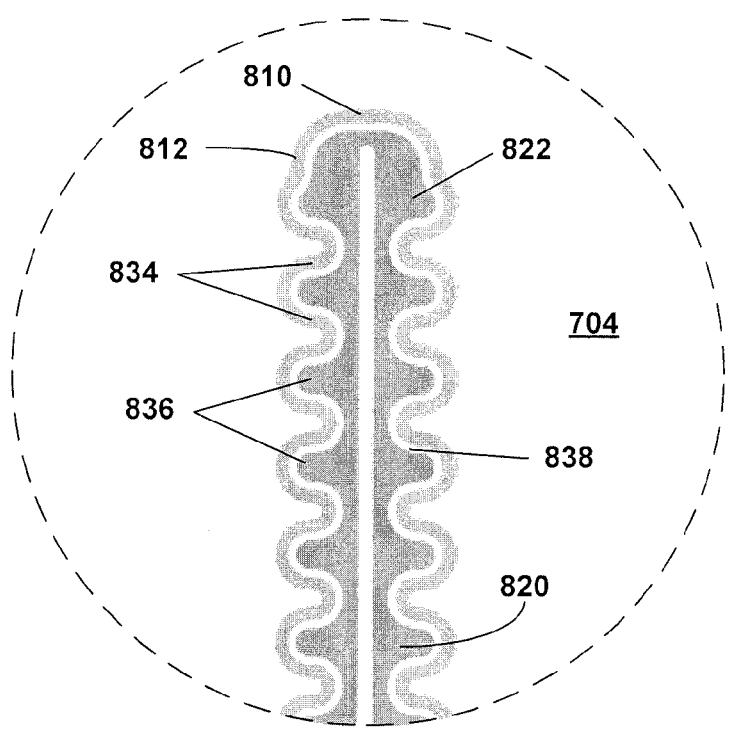
FIG. 8B is an enlarged view of a portion of the soot sensor of FIG. 7 according to another embodiment consistent with the present disclosure.

FIG. 8B is an enlarged view of a portion of the soot sensor of FIG. 7 according to another embodiment consistent with the present disclosure. In the illustrated embodiment, the sensor and heater elements 708, 718 include continuous loops 810, 820 of conductive material disposed on the first surface 704. The loops 810, 820 are arranged in a serpentine configuration including first and second sets of a plurality of undulations 812, 822. The first and second sets of plurality of undulations 812, 822 further define first and second subsets of plurality of undulations 834, 836, respectively. A plurality of gaps 838 are defined within and between each of the first and second subsets of plurality of undulations 834, 836, wherein the gaps 838 are substantially uniform in size and/or shape.

In the illustrated embodiment, the loop 810 is substantially narrower in width than the loop 710 shown in FIG. 8A, thereby increasing the resistance of loop 810 to a value greater than the resistance of loop 710. An increase in resistance may allow the loop 810 to be configured to sense temperature with greater accuracy than the loop 710.

Figure 8C:
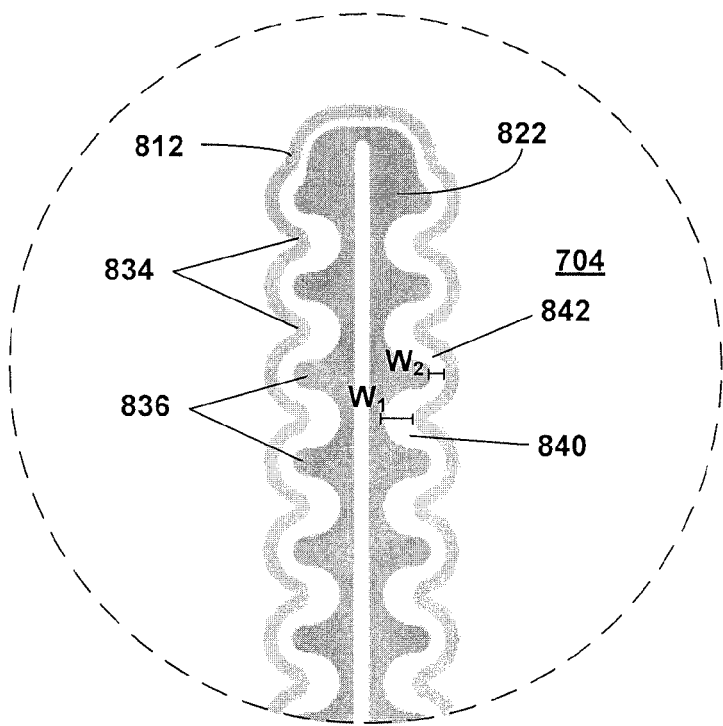
FIG. 8C is an enlarged view of the portion of the soot sensor of FIG. 7 according to another embodiment consistent with the present disclosure.

FIG. 8C is an enlarged view of a portion of the soot sensor of FIG. 7 according to another embodiment consistent with the present disclosure. In the illustrated embodiment, a plurality of gaps 840, 842 are defined within and between each of the first and second subsets of plurality of undulations 834, 836, wherein the gaps 840, 842 vary in size and/or shape. For example, gap 840 has a width $W_1$ and gap 842 has a width $W_2$, wherein width $W_1$ is generally greater than width $W_2$. The gaps 840, 842 of varying size and/or shape may allow the sensor element 708 to have a wider dynamic range of response when sensing soot particle accumulation.

Figure 9:
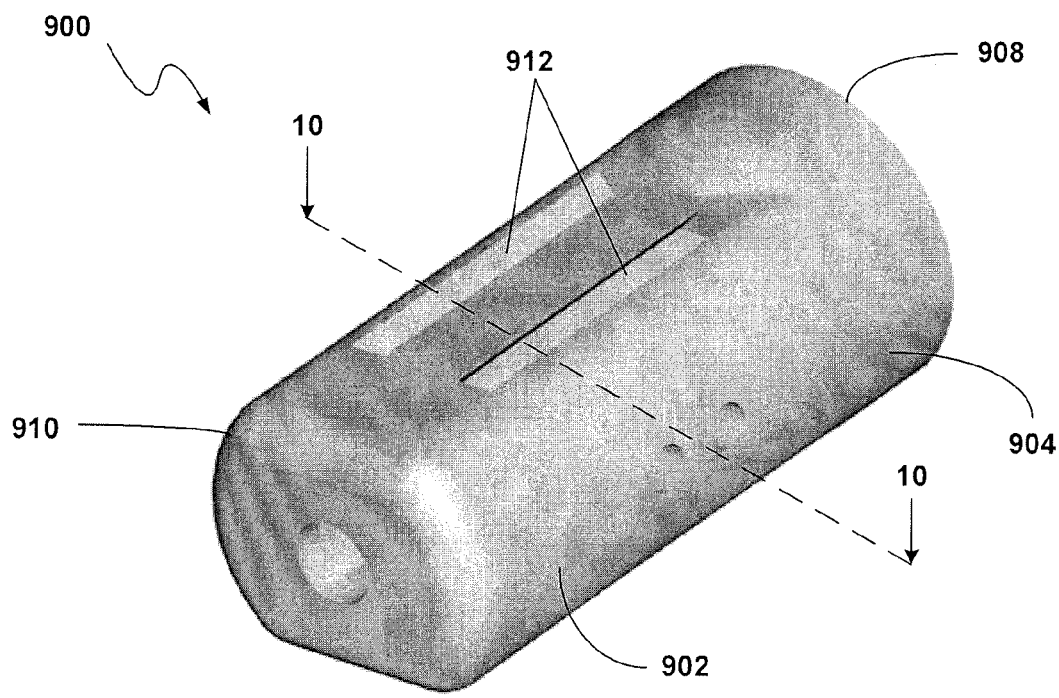
FIG. 9 is a perspective view of a soot sensor tip consistent with the present disclosure.
Figure 10:
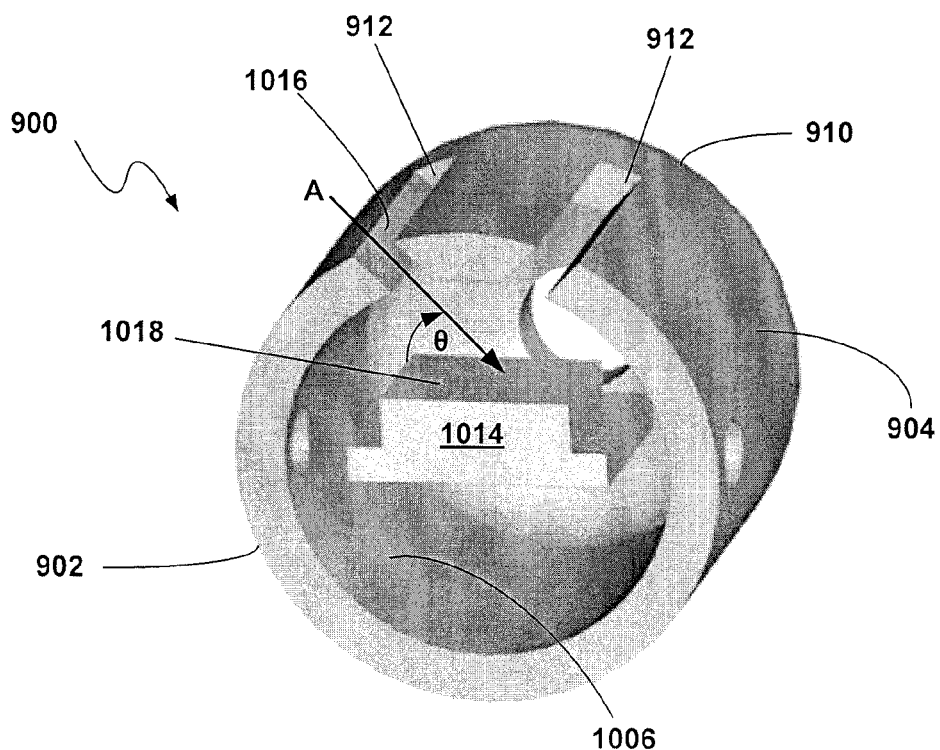
FIG. 10 is an enlarged perspective sectional view of the soot sensor tip of FIG. 9 taken along line 10-10.

FIG. 9 is perspective view of a soot sensor tip consistent with the present disclosure and FIG. 10 is an enlarged perspective sectional view of the soot sensor tip of FIG. 9 taken along line 10-10. The tip 900 is configured to at least partially enclose a soot sensor 1014, wherein the soot sensor 1014 may include embodiments consistent with the present disclosure. The tip 900 includes a body 902 having an exterior surface 904 and an interior surface 1004 and a proximal end 908 and a distal end 910. In the illustrated embodiment, the body 902 gradually transitions from a generally round shape at the proximal end 908 to a generally rectangular shape at the distal end 910. The geometry of the body 902 is configured to minimize volume on the interior of the tip 900. The body 902 defines at least one angularly disposed channel 912 defining a path 1016 from the exterior surface 904 of the body 902 to the interior surface 1006 of the body 902.

The path 1016 is configured to direct exhaust gas flow to the soot sensor 1014, and may be defined by sidewalls oriented at an angle θ of less than 90 degrees relative to the first surface 1018 of the soot sensor 1014, as indicated by the arrow A in FIG. 10. The path 1016 may thus be configured at an angle less than 90 degrees relative to the first surface 1018 to allow soot from exhaust gas flow to enter the interior of the body and impact the soot sensor 1014 at an angle less than 90 degrees relative to the first surface 1018 of the soot sensor 1014. The body 902 may define a plurality of angularly disposed channels 912 positioned along an entire circumference of the body.

Figure 11:
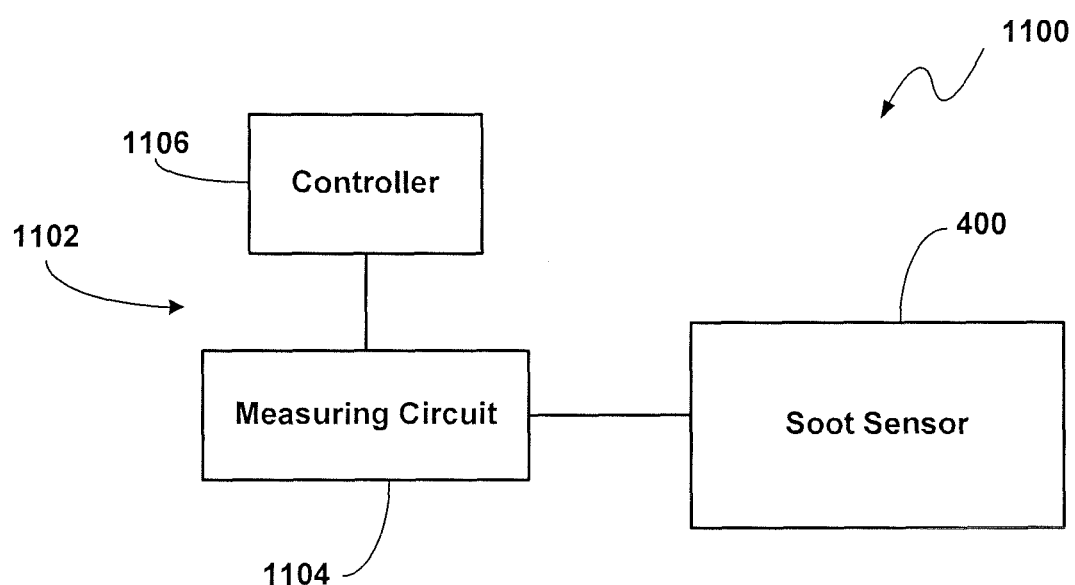
FIG. 11 is a block diagram of one exemplary embodiment of a soot sensor system consistent with the present disclosure.

FIG. 11 is a block diagram of one exemplary embodiment of a soot sensor system consistent with the present disclosure. The soot sensor system 1100 includes a soot sensor 400. For purposes of clarity and description, references will be made to the soot sensor 400 of FIG. 4. It should be noted, however, that the soot sensor system 1100 may include other embodiments of the soot sensor consistent with the present disclosure. The soot sensor system 1100 further includes circuitry 1102 electrically coupled to the soot sensor 400 and configured to provide electrical current to the soot sensor 400. In one embodiment, the circuitry 1102 may be coupled to the first and second electrical contacts 414, 416 and 424, 426 of the sensor and heater elements 408, 418, respectively, for providing currents $I_{sense}$ and/or $I_{heater}$.

The circuitry 1102 includes a measuring circuit 1104 electrically coupled and configured to communicate with a controller 1106. The measuring circuit is also electrically coupled to the soot sensor 400, e.g. to the first and second electrical contacts 414, 416 of the sensor element 408 and/or the first and second electrical contacts 424, 426 of the heater element 418. The measuring circuit 1104 may be configured to apply a voltage between first and second electrical contacts 414, 416 and provide an output to the controller 1106 representative of the resulting value of $I_{sense}$. The controller 1106 may be a known engine control unit (ECU) of an automobile and communication between the soot sensor 440, measuring circuit 1104 and the controller may be accomplished via a known CAN bus.

The value of the current $I_{sense}$ through the sensor element 408 may be utilized to determine an amount of soot that has been deposited on the soot sensor 400, which may be further indicative of an amount of soot in an exhaust stream communicating with the sensor 400. As previously noted, when soot is deposited between the first and second electrical contacts 414, 416 the electrical resistance of the conductive path between the contacts 414, 416 changes, which results in a corresponding change in $I_{sense}$. The value of $I_{sense}$ is representative of the amount of soot that has been deposited on the sensor 400.

The measuring circuit 1104 may also be configured to apply a voltage between the first and second electrical contacts 424, 426 of the heater element. When the value of $I_{sense}$ reaches a predetermined threshold, the controller 1106 may provide an output to the measuring circuit 1104 to cause the measuring circuit to activate the heater element 418 by providing a current $I_{heater}$ to the heater element 418. Upon activation of the heater element 418, the heater element 418 may heat to a temperature at which accumulated soot particles are incinerated, thereby clearing soot particles from the soot sensor 400, particularly the sensor element 408.

Additionally, the circuitry 1102 may be configured to detect open circuits and/or breaks in the sensor and/or heater elements 408, 418. For example, if the sensor element 408 has a break, the circuit between the contacts 414, 416 of the sensor element will be an open circuit or a circuit with higher-than-normal resistance. Thus, if the current $I_{sense}$ falls below a predetermined threshold, the controller 1106 may provide an output indicating failure in the sensor element.

Figure 12:
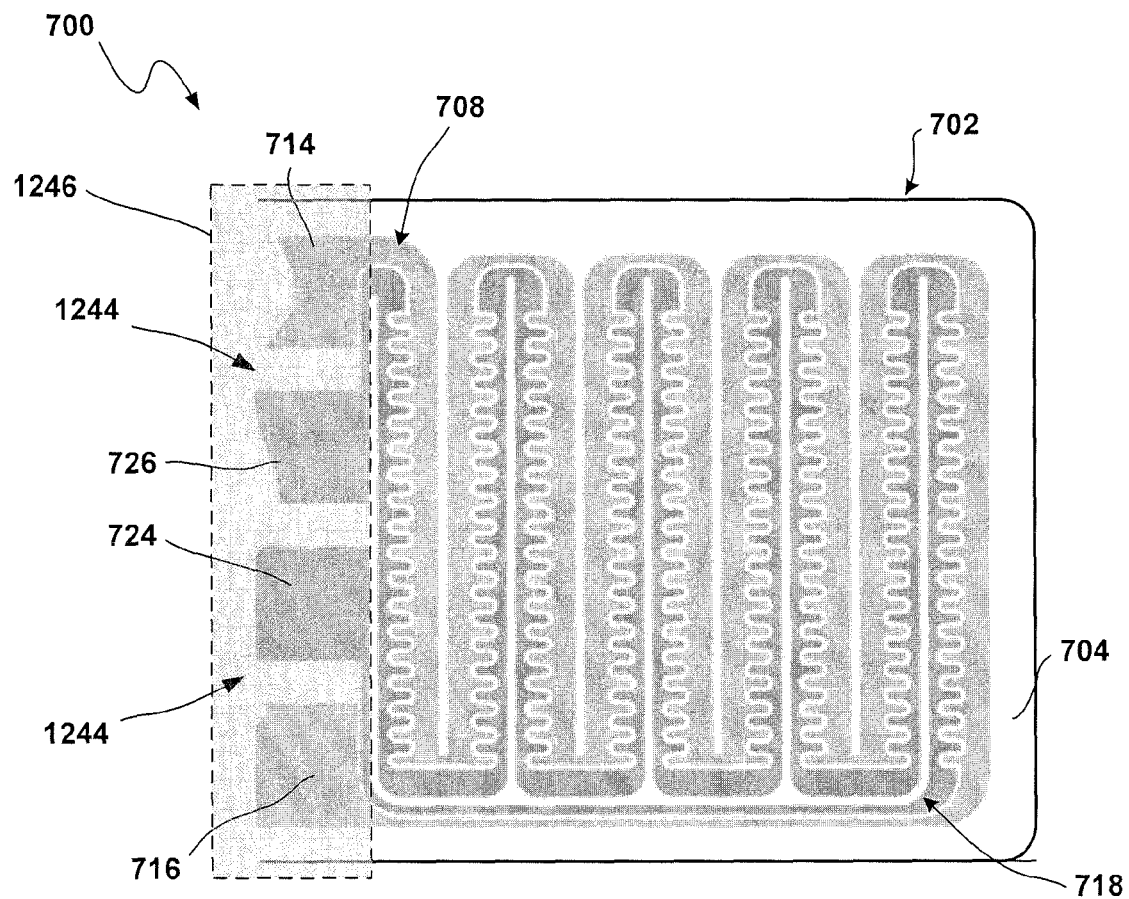
FIG. 12 is a schematic top view of the soot sensor of FIG. 7 including a passivation layer.

FIG. 12 is a schematic top view of the soot sensor of FIG. 7 including a passivation layer. In the illustrated embodiment, the soot sensor 700 may include a pad portion 1244 defining at least the first 714 and second 716 electrical contacts of the sensor element 708 and/or the first 724 and second 726 electrical contacts of the heater element 718. The soot sensor 700 may further include a passivation layer 1246 disposed on the first surface 704 of the substrate 702 and at least over the pad portion 1244. The passivation layer 1246 may be configured to inhibit and/or prevent any conduction between the first 714 and second 716 electrical contacts of the sensor element 708 and/or between the first 724 and second 726 electrical contacts of the heater element 718. Additionally, the passivation layer 1246 may be configured to inhibit and/or prevent the occurrence of high heat. The passivation layer 1246 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication. Additionally, the passivation layer 1246 may include materials configured to provide thermal insulation. In the illustrated embodiment, the passivation layer 1246 may include a thick film glass.

Figure 13:
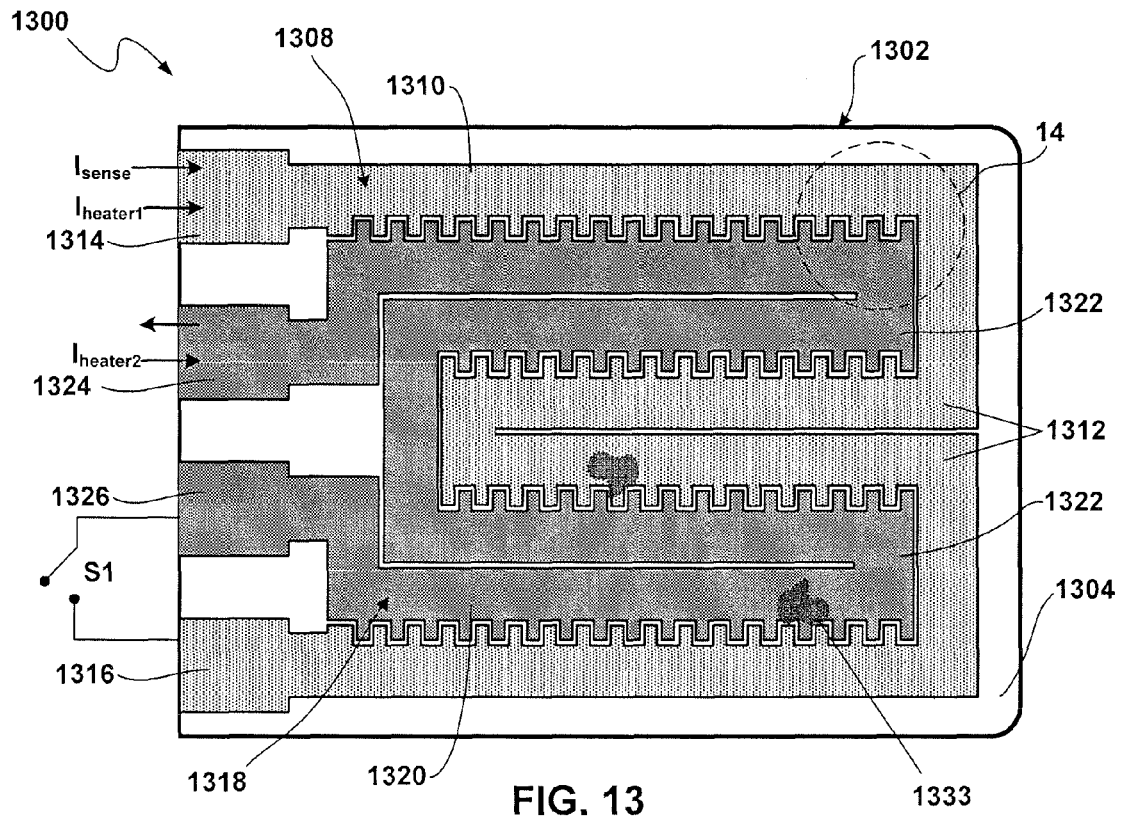
FIG. 13 is a schematic top view of another embodiment of a soot sensor consistent with the present disclosure.
Figure 14:
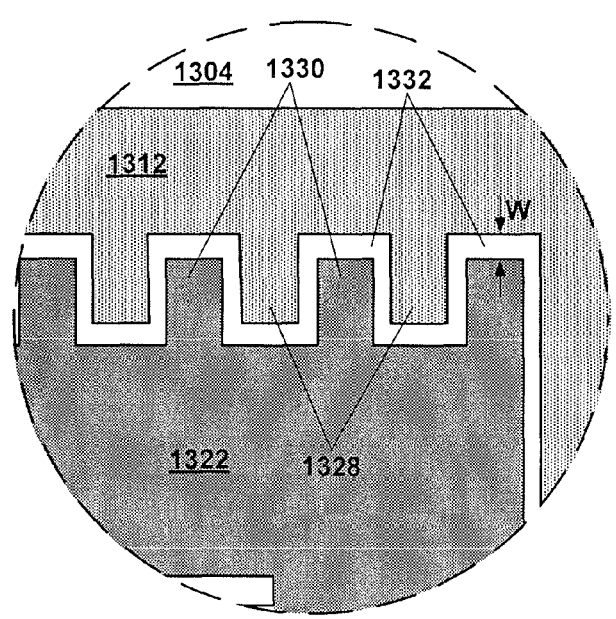
FIG. 14 is an enlarged view of a portion of the soot sensor of FIG. 13.

FIG. 13 is a schematic top view of another embodiment of a soot sensor 1300 consistent with the present disclosure and FIG. 14 is an enlarged view of a portion of the soot sensor 1300 of FIG. 13. Generally, the soot sensor 1300 includes a substrate 1302 defining a first surface 1304. A first sensor/heater element 1308 and a second sensor/heater element 1318 are formed on the first surface 1304. As described in greater detail herein, the first and second sensor/heater elements 1308, 1318 may each be configured to sense soot accumulation in a similar manner as the sensor element 408 shown in FIG. 4. Additionally, the first and second sensor/heater elements 1308, 1318 may each be configured to heat and at least partially remove, e.g. incinerate, accumulated soot, thereby cleaning/regenerating the sensor 1300 for continued use.

The first and second sensor/heater elements 1308, 1318 each include at least one continuous loop of conductive material 1310, 1320, respectively, disposed on the substrate 1302. Similar to the embodiment of FIG. 4, the loops 1310, 1320 may be arranged in a serpentine configuration including first and second sets of undulations 1312, 1322, respectively. Referring to FIG. 14, the first and second sets of undulations 1312, 1322 further define first 1328 and second 1330 subsets of undulations, respectively. A plurality of gaps 1332 are defined within and between each of the first 1328 and second 1330 subsets of plurality of undulations. As shown, the gaps 1332 may have a substantially uniform size and/or shape. In the illustrated embodiment, the gaps 1332 may have a width W. The width W of the gaps 1332 may range from 10 microns to 100 microns. In one embodiment, the width W of the gaps 1332 is 20 microns. It should be noted that some of the plurality of gaps 1332 may vary size and/or shape, thereby allowing the sensor/heater elements 1308, 1318 to have a wider dynamic range of response when sensing soot particle accumulation.

As shown, the first sensor/heater element 1308 includes first 1314 and second 1316 electrical contacts at opposite ends of the loop 1310. The first and second electrical contacts 1314, 1316 may be configured for coupling to circuitry for providing current through the loop 1310. Similarly, the second sensor/heater element 1318 includes first 1324 and second 1326 electrical contacts at opposite ends of the loop 1320. The first and second electrical contacts 1324, 1326 may be configured for coupling to circuitry for providing current through the loop 1320.

The first and second sensor/heater elements 1308, 1318 may include electrically conductive materials or metals, such as, alumina, gold, platinum, osmium, rhodium, iridium, ruthenium, aluminum, titanium, zirconium, and the like, as well as, oxides, alloys, and combinations including at least one of the foregoing metals. In one embodiment, the elements 1308, 1318 may include alumina having a film platinum trace deposited on a portion thereof.

The substrate 1302 may include a non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and providing structural integrity and/or physical protection. Additionally, the soot sensor 1300 may include thick film and/or thin film constructions.

As described in greater detail herein, the soot sensor 1300 may be configured to operate in a first mode (hereinafter referred to as "soot sensing mode"), wherein the first and second sensor/heater elements 1308, 1318 are configured to sense soot accumulation on at least the first surface 1304 of the soot sensor 1300. The soot sensor 1300 may be further configured to operate in a second mode (hereinafter referred to as "regeneration mode"), wherein the first and second sensor/heater elements 1308, 1318 are configured to heat and remove (e.g. incinerate) at least a portion of accumulated soot on the first surface 1304, thereby cleaning/regenerating the sensor 1300.

The first and second sensor/heater elements 1308, 1318 may be configured to operate separately and independently from one another, as described in regards to the embodiment of FIG. 4. Additionally, the soot sensor 1300 may further include a switch S1 coupled to the second electrical contacts 1316, 1326 of the first and second sensor/heater elements 1308, 1318, respectively, for selectively coupling and decoupling the contacts 1316, 1326. For example, when the switch S1 is open, the first and second sensor/heater elements 1308, 1318 may operate separately from one another. When the switch S1 is closed, the first and second sensor/heater elements 1308, 1318 may be electrically coupled to one another, establishing a continuous loop of conductive material between contacts 1314 and 1324.

Figure 15:
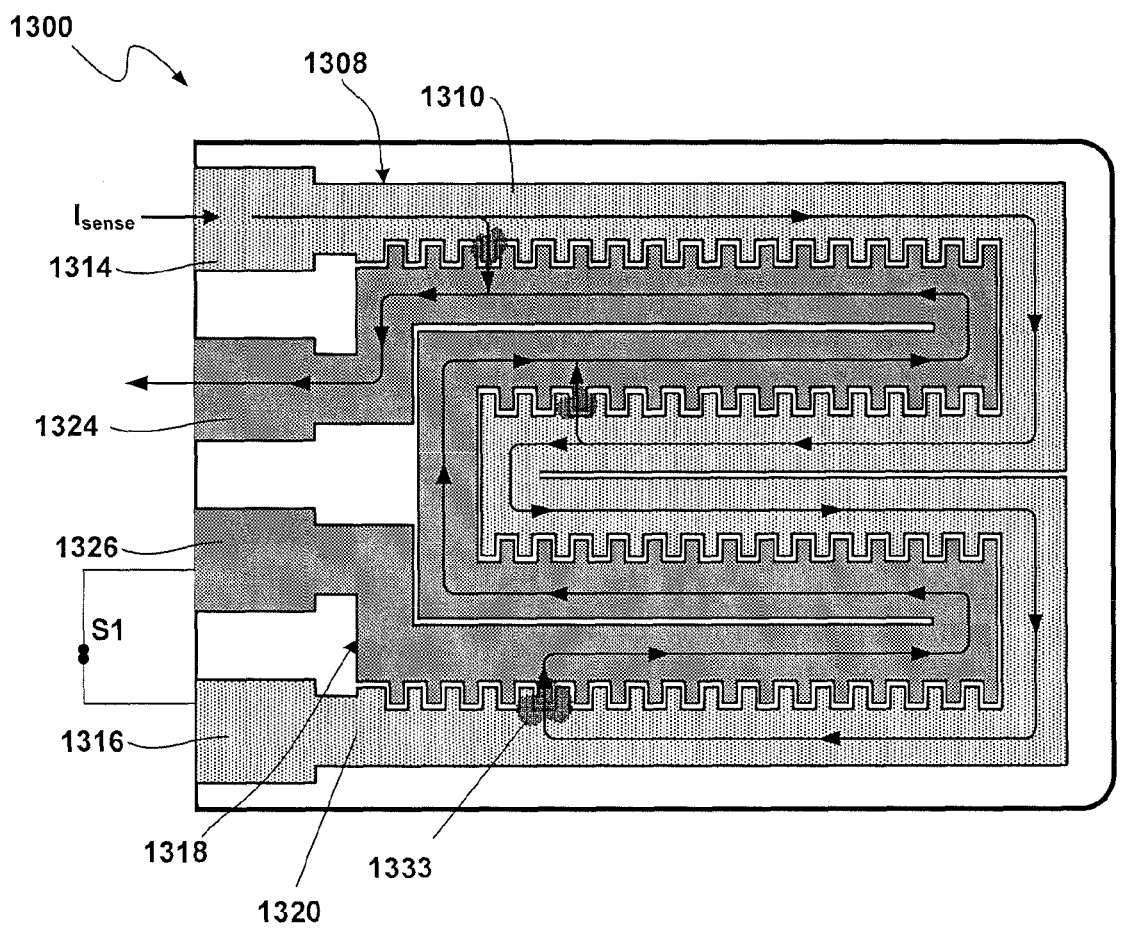
FIG. 15 is a schematic top view of the soot sensor of FIG. 13 in a soot sensing mode.

When the sensor 1300 is in the soot sensing mode, as shown in FIG. 15, an input current $I_{sense}$ may be provided at the first electrical contact 1314 (or second electrical 1316 contact). The value of $I_{sense}$ may be representative of the amount of soot disposed on the sensor 1300. As shown in FIG. 15, when the switch S1 is closed, the first and second sensor/heater elements 1308, 1310 are electrically coupled to one another and establish a continuous loop of conductive material between contacts 1314 and 1324. The current $I_{sense}$ may then pass through both the first sensor/heater element 1308 and second sensor/heater element 1318 to allow both the first and second sensor/heater elements 1308, 1318 to act as a single sensor element. Soot particles 1333 are shown as accumulated on the first surface 1304 of the substrate 1302, including on the first and second sensor/heater elements 1308, 1318. As soot 1333 builds up on the sensor/heater elements 1308, 1318, the resistance of the continuous loop (e.g. made of loops 1310 and 1320) changes, which changes the value of $I_{sense}$. The value of $I_{sense}$ is thus representative of the amount of soot accumulated on the sensor.

Figure 16:
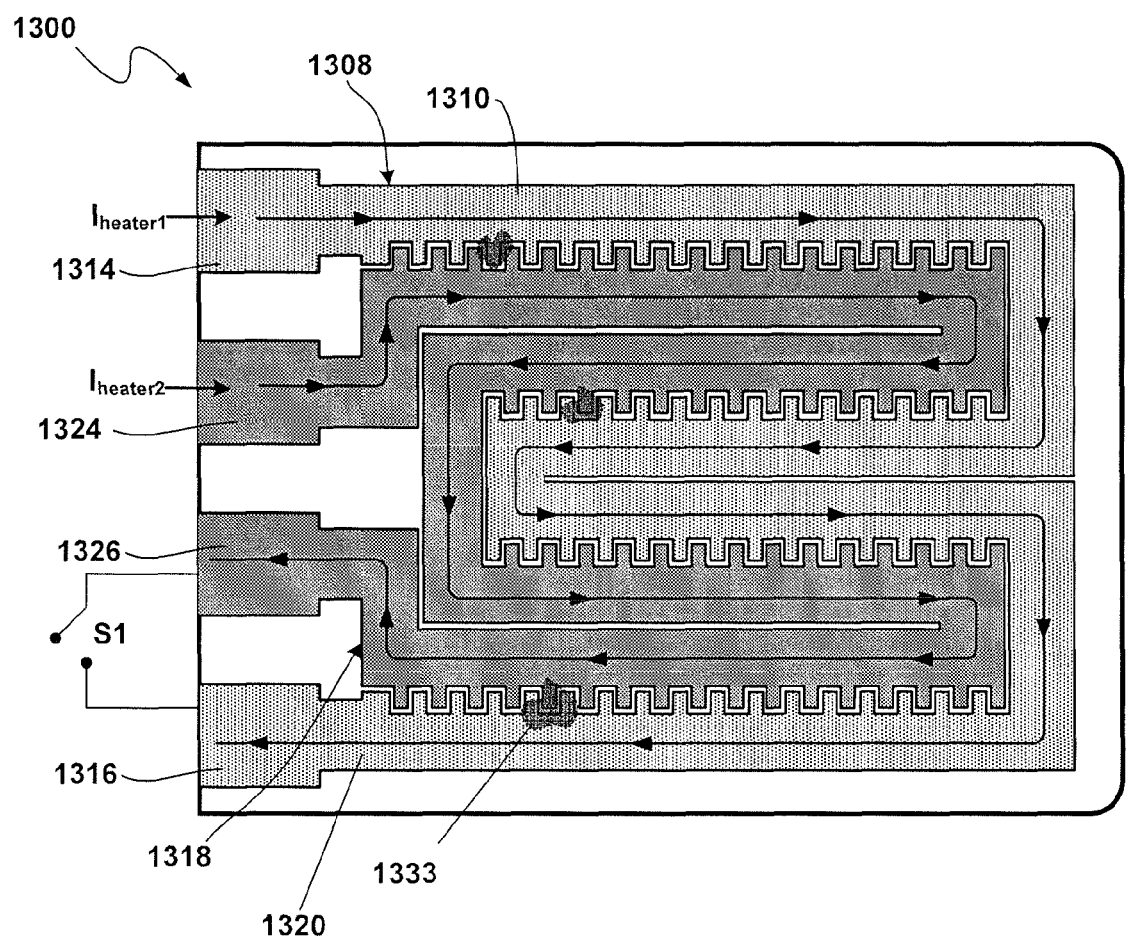
FIG. 16 is a schematic top view of the soot sensor of FIG. 13 in a regeneration mode.
Figure 17A:
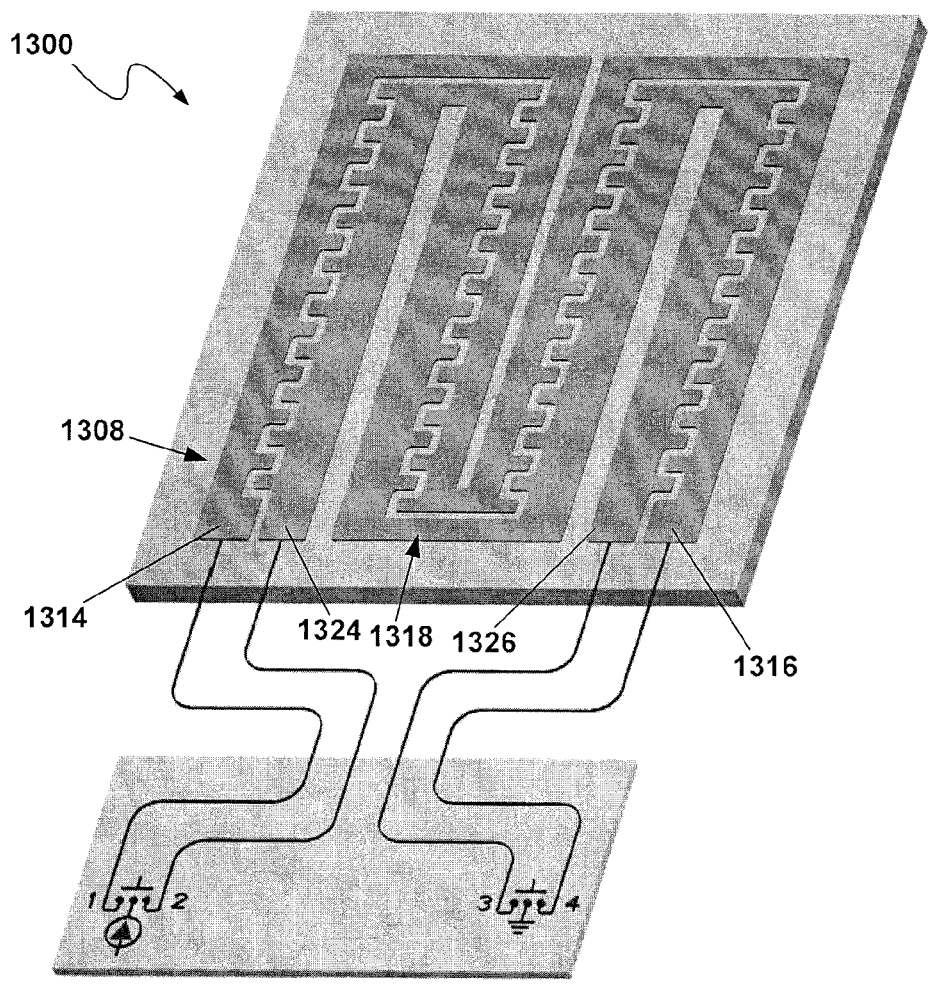
FIGS. 17A-17D are schematic top views and associated circuitry of the soot sensor of FIG. 13 in first and second regeneration modes.
Figure 17B:
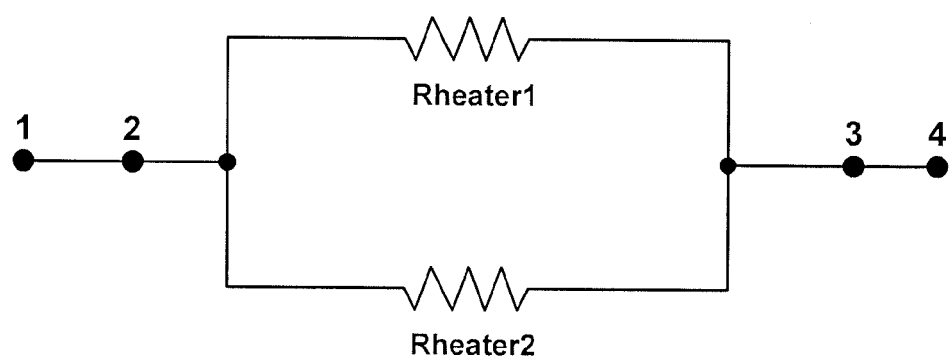

When a threshold amount of soot 1333 accumulates on the first and second sensor/heater elements 1308, 1318, e.g. as determined by reaching a threshold value of $I_{sense}$, the soot sensor 1300 may be configured to enter the regeneration mode, as shown in FIGS. 16 and 17A-17B. As shown in FIG. 16, when the sensor 1300 is in the regeneration mode, an input current $I_{heater1}$ may be provided at the first electrical contact 1314 (or second electrical 1316 contact) of the first sensor/heater element 1308. Similarly, an input current $I_{heater2}$ may be provided at the first electrical contact 1324 (or second electrical 1326 contact) of the second sensor/heater element 1318. In one embodiment, when a threshold amount of soot 1333 accumulates on the first and second sensor/heater elements 1308, 1318, e.g. as determined by reaching a threshold value of $I_{sense}$, the heater currents $I_{heater1}$ and/or $I_{heater2}$ may be applied to cause the corresponding first and second sensor/ heater elements 1308, 1318 to heat and at least partially remove, e.g. incinerate, the soot 433, thereby cleaning/regenerating the sensor 1300 for continued use.

In one embodiment, when the switch S1 is open, the first and second sensor/heater elements 1308, 1318 may operate independently of one another, wherein the heater current $I_{heater1}$ may be applied to cause only the first sensor/heater element 1308 to heat up. Similarly, the heater current $I_{heater2}$ may be applied to cause only the second sensor/heater element 1318 to heat up. When the switch S1 is closed, loops 1310 and 1320 are electrically coupled to one another establishing a single continuous loop of conductive material between the contacts 1314 and 1324. The current $I_{heater1}$ may then pass through both the first sensor/heater element 1308 and second sensor/heater element 1318 to allow both elements 1308, 1318 to act as a single heater element and heat up.

The soot sensor 1300 may be configured to operate in a first regeneration mode and a second regeneration mode, as shown in FIGS. 17A-17D. FIG. 17A illustrates the soot sensor 1300 in a first generation mode and 17B illustrates a schematic view of the circuitry associated with the soot sensor 1300 in the first generation mode. As shown, when in a first regeneration mode, the first and second sensor/heater elements 1308, 1318 may be arranged in parallel with one another. This configuration may be suitable for situations in which the first and second sensor/heater elements 1308, 1318 are hot and the resistance is high, thereby necessitating a need to pass more input current into the elements 1308, 1318 to increase heating of the elements 1308, 1318 during high flow conditions.

Figure 17C:
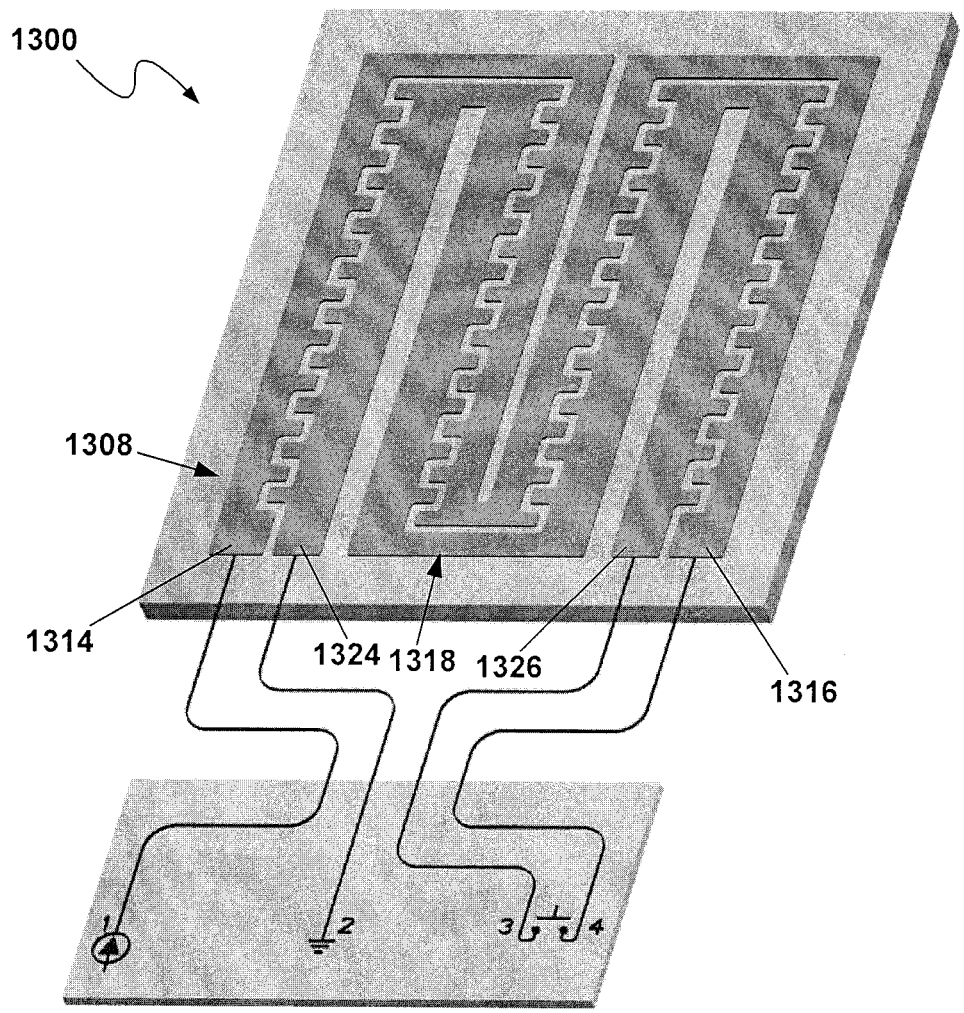
Figure 17D:
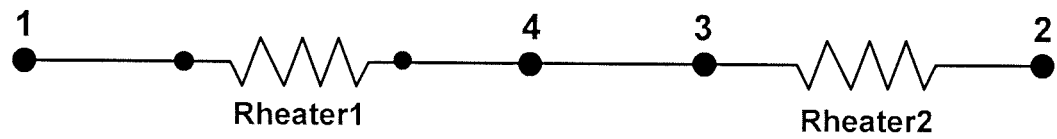

FIG. 17C illustrates the soot sensor 1300 in a second generation mode and 17D illustrates a schematic view of the circuitry associated with the soot sensor 1300 in the second generation mode. As shown, when in a second regeneration mode, the first and second sensor/heater elements 1308, 1318 may be arranged in series with one another. Arrangement of the first and second sensor/heater elements 1308, 1318 in a series generally results in a higher resistance than the resistance of a parallel arrangement (shown in FIG. 17A). Thus, operating in the second regeneration mode (e.g. series configuration) may be suitable for situations in which it is desirable to limit current consumption and/or when the first and second sensor/heater elements 1308, 1318 are cold and rapid heating is desired. Additionally, a higher resistance may also provide an improved temperature measurement of the elements 1308, 1318 during regeneration due to higher resolution. It should be noted that the first and second regeneration modes may be controlled under solid state switching and software control. Accordingly, in some embodiments consistent with the present disclosure, the soot sensor may be configured to provide staged heating, wherein operation of the elements 1308, 1318 in the first and/or second regeneration modes may be controlled (e.g. start, stop, pause, change between modes, etc.) in real-time or near real-time to account for exhaust flow velocity and/or exhaust temperature.

Figure 18:
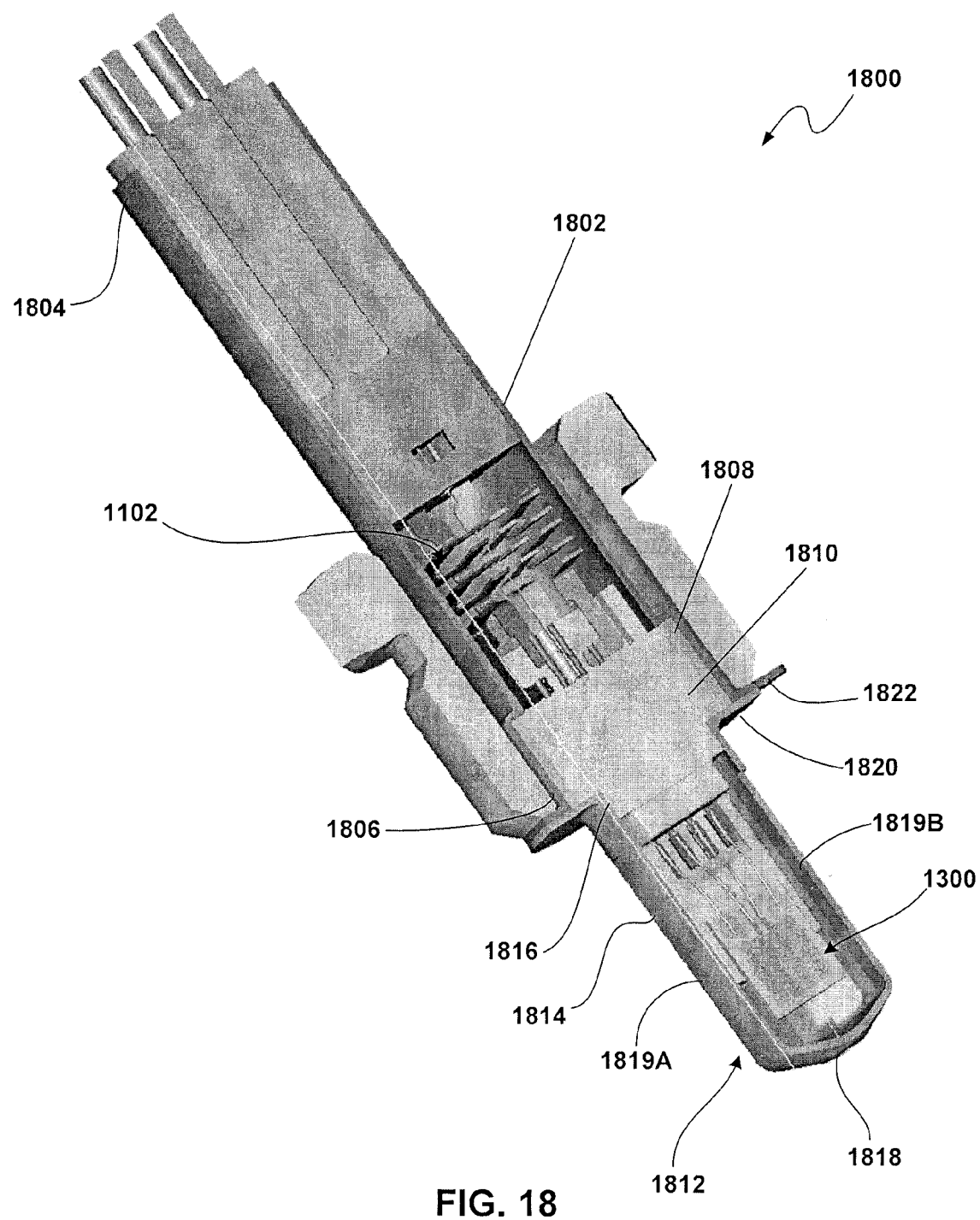
FIG. 18 is a perspective sectional view of a soot sensor assembly consistent with the present disclosure.

FIG. 18 is a perspective sectional view of one embodiment of a soot sensor assembly 1800 consistent with the present disclosure. Generally, the soot sensor assembly 1800 includes a housing 1802 having a first end 1804 and a second 1806. The housing 1802 is shaped and/or sized to partially enclose a slug insert 1810. The housing 1802 may include metal and/or non-metal material. As shown, the second end 1806 of the housing 1802 is shaped and/or sized to receive a portion of the slug insert 1810 and retain the slug insert 1810 by way of a ring 1808 coupled to at least a portion of the slug insert 1810. The ring 1808 may be coupled to the housing 1802 by various methods known to those skilled in the art. In one embodiment, the ring 1808 may be laser welded to the housing 1802, thereby providing a hermetic seal between the housing 1802 and ring 1808 (e.g. substantially impervious to air and/or gas).

The soot sensor assembly 1800 further includes a soot sensor 1300 coupled to the slug insert 1810. For purposes of clarity and description, references will be made to the soot sensor 1300 of FIG. 13. It should be noted, however, that the soot sensor assembly 1800 may include other embodiments of a soot sensor consistent with the present disclosure. The soot sensor assembly 1800 further includes a sensor tip 1812 coupled to at least the housing 1802 and configured to at least partially enclose the soot sensor 1300. The sensor tip 1812 includes a body 1814 having an open proximal end 1816 and a closed distal end 1818. The body 1814 includes an exterior surface 1819A and an interior surface 1819B.

In the illustrated embodiment, the proximal end 1816 of the sensor tip 1812 may define a flange portion 1820 configured to engagingly mate with a flange portion 1822 of the second end 1806 of the housing 1802. The sensor tip 1812 may be coupled to at least the housing 1802 at the respective flange portions 1820, 1822, wherein the flange portions 1820, 1822 may be sealed to one another. Additionally, the housing 1802 may be configured to partially enclose circuitry 1102 electrically coupled to the soot sensor 1300 and configured to provide electrical current to the soot sensor 1300.

Figure 19A:
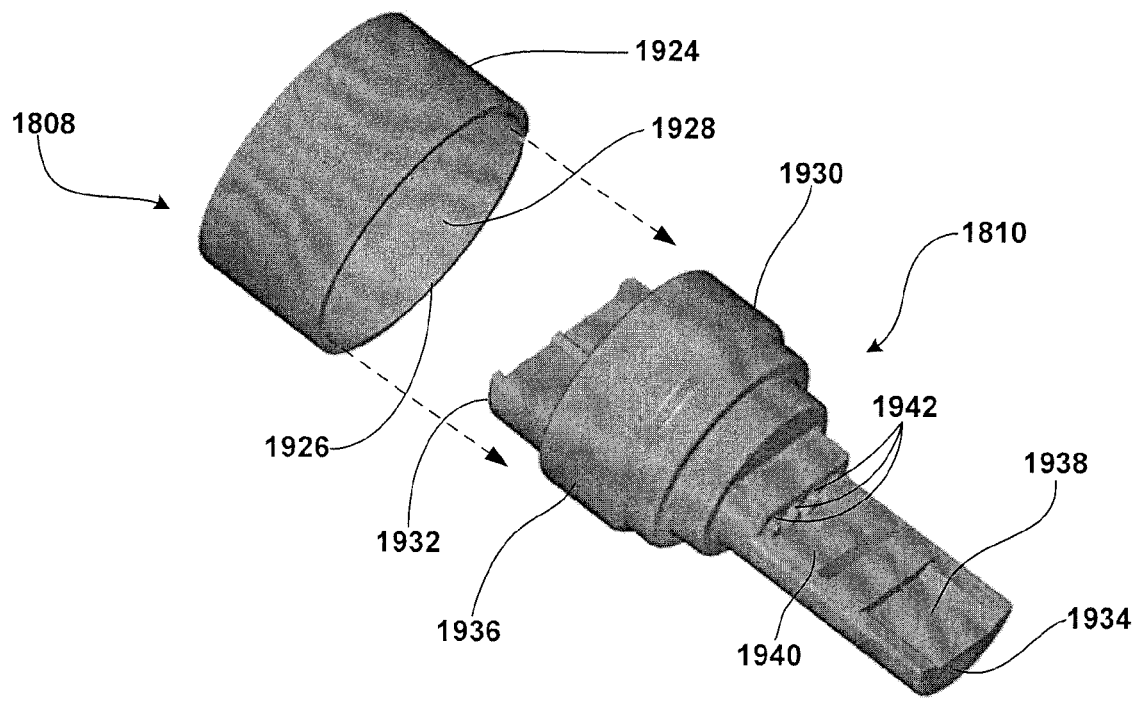
FIGS. 19A-19B are perspective views of embodiments of the soot sensor assembly of FIG. 18.
Figure 19B:
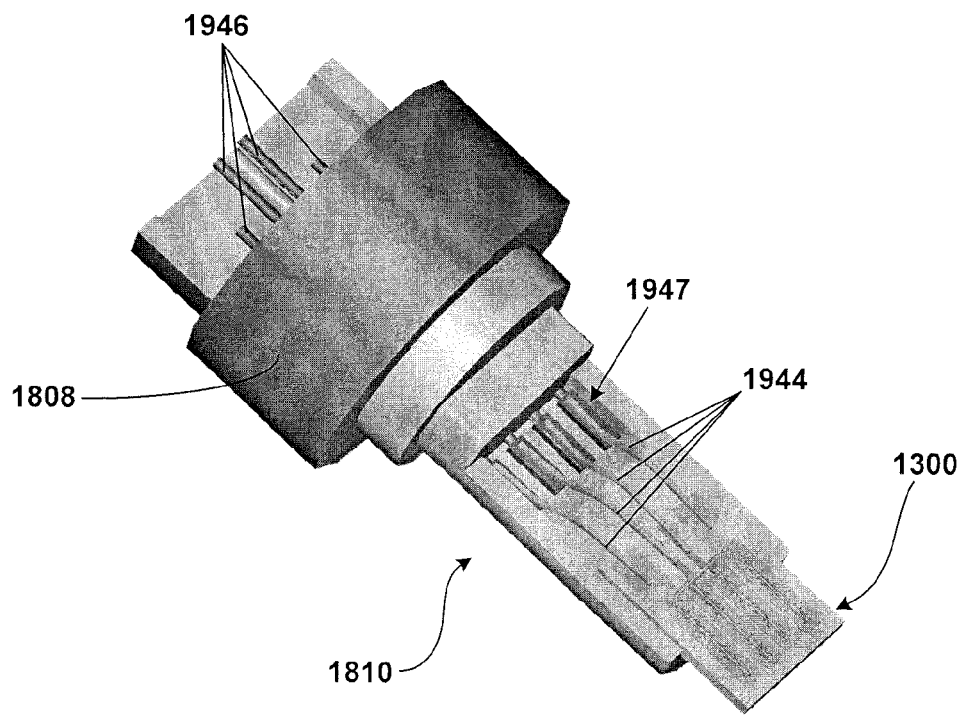

FIGS. 19A-19B are perspective views of the slug insert 1810 of the soot sensor assembly 1800 of FIG. 18. FIG. 19A illustrates the slug insert 1810 separated from the ring 1808 and FIG. 19B illustrates the slug insert 1810 coupled to the ring 1808. The ring 1808 may include a body 1924 defining an interior surface 1928 and a periphery 1926 having a circumference. The ring 1808 may be configured to receive at least a portion of the slug insert 1810. The ring 1808 may include metal and/or non-metal materials.

In the illustrated embodiment, the slug insert 1810 includes a body 1930 having a proximal end 1932 and a distal end 1934. The body 1930 also includes a discrete portion 1936 having a circumference less than the circumference of the periphery 1926 of the ring 1808, such that the discrete portion 1930 is configured to fit within the ring 1808 and be coupled to the interior surface 1928. The discrete portion 1936 of the slug insert 1810 may be coupled to the interior surface 1928 of the ring 1808 by various methods known to those skilled in the art. In one embodiment, for example, the discrete portion 1936 of the slug insert 1810 may be joined to the interior surface 1928 of the ring 1808 by a brazing method, thereby providing a substantially hermetic seal between the slug insert 1810 and the ring 1808.

The body 1930 of the slug insert 1810 also includes a first surface 1938 configured to support at least a portion of the soot sensor 1300 and a second surface 1940 configured to support electrical connections, e.g. interconnect wires 1946 coupled to leads 1944, as indicated by arrow 1947, of the soot sensor 1300. The body 1930 further includes apertures 1942 passing from at least the second surface 1940 through the body 1930 and to the proximal end 1932 of the slug insert 1810. The apertures 1942 are configured to receive and to allow the interconnect wires 1946 to pass from circuitry 1102 in the housing 1802 through a portion of the slug insert 1810 (e.g. body 1930) to the second surface 1940.

The first surface 1938 may define a channel shaped and/or sized to receive at least a portion of the soot sensor 1300. The first surface 1938 may further be configured to provide minimal contact with the soot sensor and to prevent heat loss during soot sensor regeneration process (heating of heater element(s)). The sensor element 1300 may be sealed to the first surface 1938 with glass, thereby increasing durability of the soot sensor 1300 during production assembly and decreasing vibration tendency. As appreciated by one skilled in the art, the soot sensor 1300 may be coupled to the first surface 1938 by other known methods.

As shown, the second surface 1940 may define a channel shaped and/or sized to receive a portion of the lead wires 1944 and associated interconnect wires 1946 coupled thereto. The apertures 1942 having interconnect wires 1946 passing therethrough may be filled with a sealant, such as glass, thereby providing a hermetic seal between the interconnect wires 1946 and the associated apertures 1942.

The slug insert 1810 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication. In the illustrated embodiment, the slug insert 1810 may include a ceramic material.

Figure 19C:
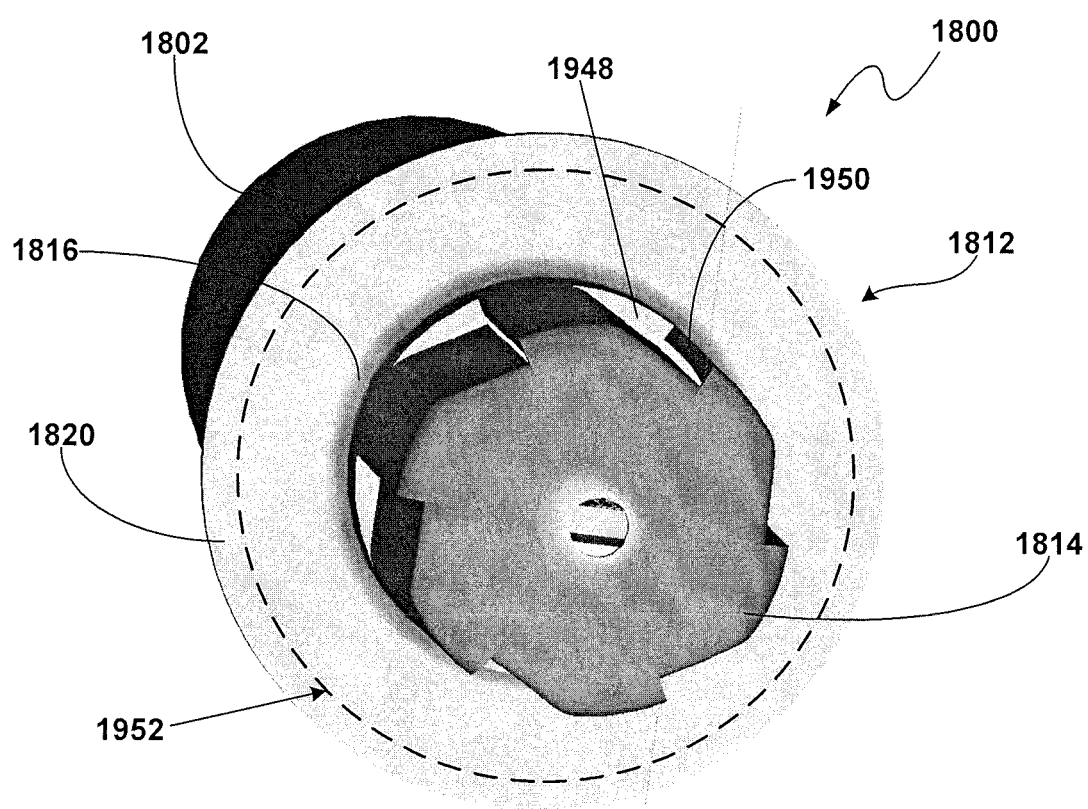
FIG. 19C is an enlarged perspective view of a portion of the soot sensor assembly of FIG. 18.

FIG. 19C is an enlarged perspective view of a portion of the soot sensor assembly 1800 of FIG. 18. As described earlier, the soot sensor assembly 1800 may include a sensor tip 1812 coupled to at least the housing 1802 and configured to at least partially enclose the soot sensor 1300. In the illustrated embodiment, the body 1814 of the sensor tip defines at least one angularly disposed channel 1948 defining a path 1950 from the exterior surface 1819A of the body 1814 to the interior surface 1819B of the body 1814. Similar to the embodiment of FIG. 9, the path 1950 is configured to direct exhaust flow to the soot sensor 1300. In the illustrated embodiment, the body 1814 of the sensor tip 1812 defines a plurality of angularly disposed channels 1948 positioned along an entire circumference of the body 1814. It should be noted that the soot sensor assembly 1800 may include other embodiments of a sensor tip consistent with the present disclosure.

In the illustrated embodiment, the proximal end 1816 of the sensor tip 1812 may define a flange portion 1820. The flange portion 1820 is configured to engagingly mate with the flange portion 1822 of the second end 1806 of the housing 1802. The flange portion 1820 of the sensor tip 1812 may be laser beam welded to the flange portion 1822 of the housing 1802, thereby providing a hermetic seal, as indicated by arrow 1952. As one skilled in the art would readily appreciate, the flange portions 1820, 1822 may be coupled to one another by other known methods.

Figure 20:
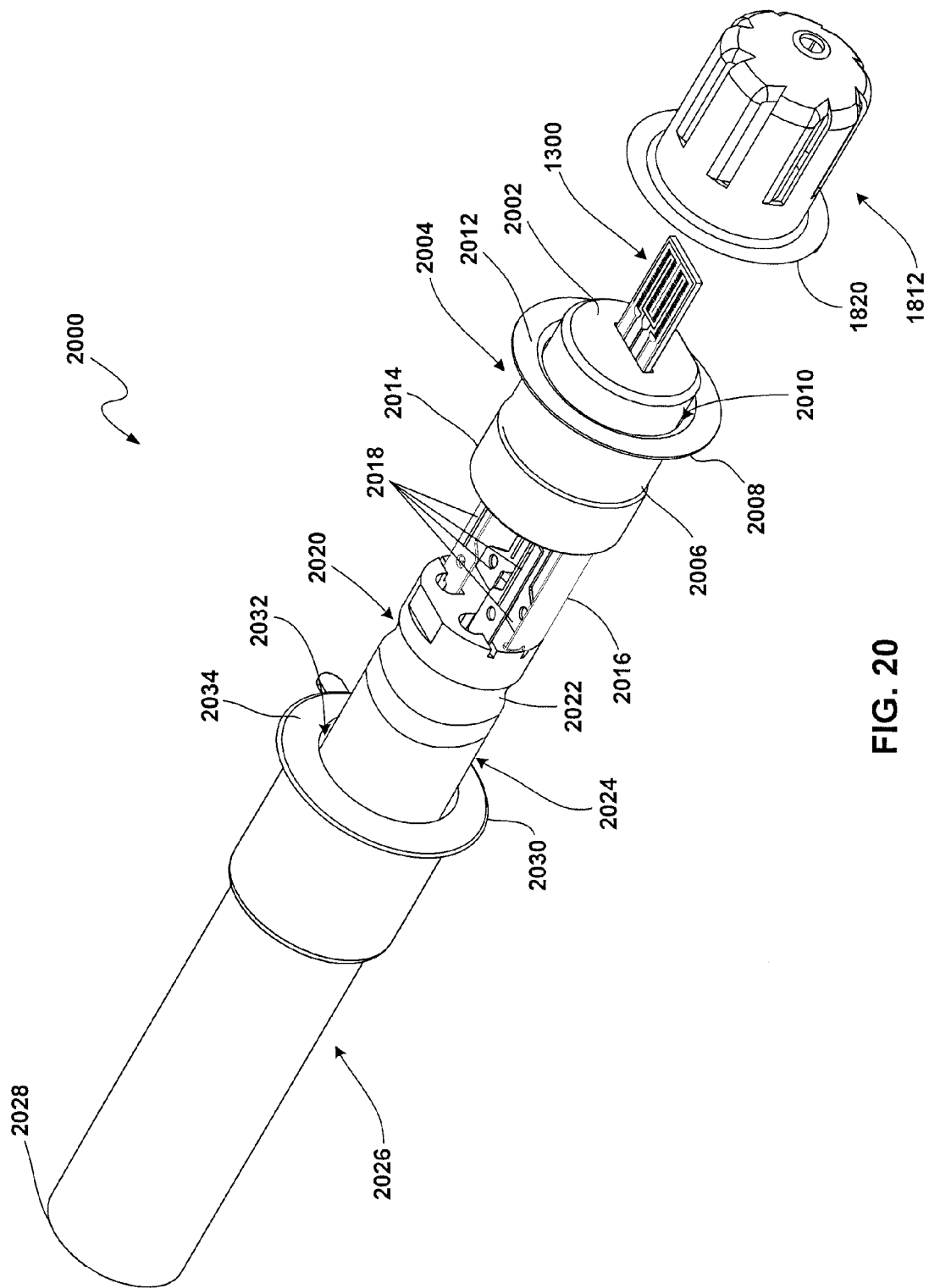
FIG. 20 is a perspective exploded view of another soot sensor assembly consistent with the present disclosure.
Figure 21:
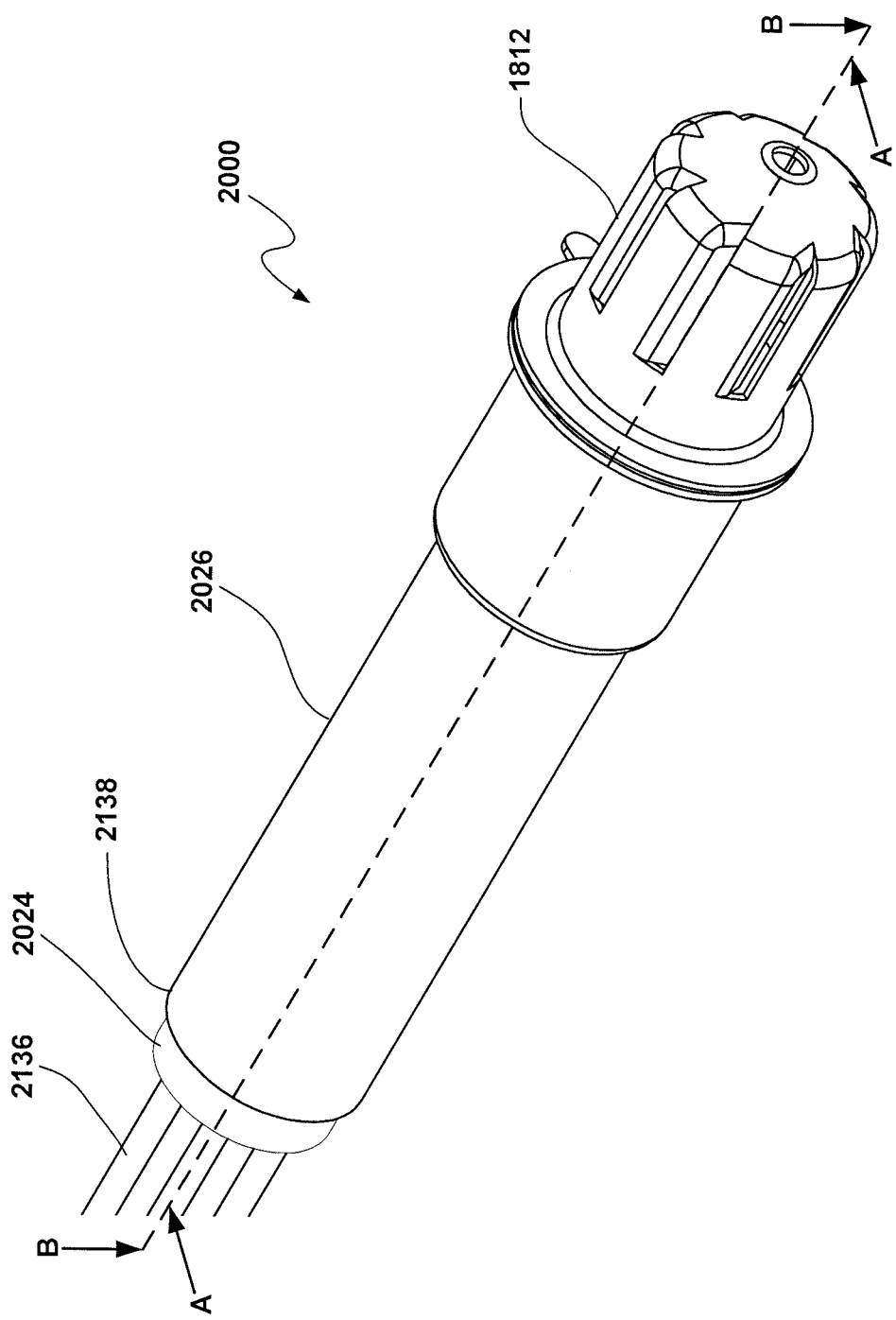
FIG. 21 is a perspective view of the soot sensor assembly of FIG. 20 in an assembled state.

FIG. 20 is a perspective exploded view of another soot sensor assembly 2000 consistent with the present disclosure and FIG. 21 is a perspective view of the soot sensor assembly 2000 of FIG. 20 in an assembled state. Generally, the soot sensor assembly 2000 includes an insulating member 2002 configured to receive and retain a portion of a soot sensor. For purposes of clarity and description, references will be made to the soot sensor 1300 of FIG. 13. It should be noted, however, that the soot sensor assembly 2000 may include other embodiments of a soot sensor consistent with the present disclosure. The insulating member 2002 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication and/or withstanding relatively high temperatures (e.g., 600° C.). In the illustrated embodiment, the insulating member 2002 may include a ceramic material.

As shown, the assembly 2000 further includes an inner housing member 2004 having a first end 2006 and a second end 2008 and a longitudinally disposed passageway 2010 extending from the first end 2006 to the second end 2008. The passageway 2010 is shaped and/or sized to receive a portion of the insulating member 2002 within. As described in greater detail herein, the inner housing member 2004 may be shaped and/or sized to receive one or more materials configured to secure lead wires (shown in FIGS. 22A-22B) in a relatively fixed position.

As shown, the soot sensor assembly 2000 further includes a sensor tip configured to be coupled to a portion of the inner housing member 2004. For purposes of clarity and description, references will be made to the sensor tip 1812 of FIG. 18. It should be noted, however, that the soot sensor assembly 2000 may include other embodiments of a sensor tip consistent with the present disclosure. The sensor tip 1812 may be coupled to at least the inner housing member 2004 and is configured to partially enclose the soot sensor 1300. In the illustrated embodiment, the flange portion 1820 of the sensor tip 1812 is configured to engagingly mate with a flange portion 2012 defined on the second end 2008 of the inner housing member 2004. The sensor tip 1812 may be coupled to at least the inner housing member 2004 at the respective flange portions 1820, 2012, wherein the flange portions 1820, 2012 may be sealed to one another.

The assembly 2000 further includes a first spacing member 2014 positioned adjacent the first end 2006 of the inner housing member 2002. The size (e.g. width) of the first spacing member 2014 may depend on the desired length of the lead wires, for example. The soot sensor assembly 2000 further includes a second spacing member 2016 positioned adjacent the spacing member 2016. For purposes of clarity, the second spacing member 2016 is illustrated partly in section. The size (e.g. width) of the second spacing member 2016 may depend on the desired length of the terminals 2018, for example. The first and second spacing members 2014, 2016 may include non-conductive and/or electrically insulating materials. Materials may include oxides, including, but not limited to, alumina, zirconia, yttria, lanthanum oxide, silica, and/or combinations including at least one of the foregoing, or any like material capable of inhibiting electrical communication. In the illustrated embodiment, the first and/or second spacing members 2014, 2016 may include a ceramic material.

The soot sensor assembly 2000 further includes a strain relief nugget 2020 configured to receive and retain a portion of each of the terminals 2018 therein. The nugget 2020 may further be coupled to a wire harness assembly 2136 (shown in FIG. 21). As shown, the nugget 2020 may include one or more passageways for each terminal 2018 to be received within. The nugget 2020 may include two complementary halves, wherein, when positioned adjacent and complementary to one another, they combine to form a unitary nugget 2020, as shown. The nugget 2020 may further include a radial groove 2022 defined on a portion thereof. The groove 2022 may provide a clearance (e.g. space) to allow a portion of the outer housing member 2026 to be crimped inwardly towards the nugget 2020 such that the crimped portion of outer housing member 2026 applies little or no force upon the nugget 2020.

The nugget 2020 may be configured to provide strain relief for connections (e.g. welds) coupling the wires of the wire harness assembly 2136 to the terminals 2018. For example, the nugget 2020 may provide strain relief if the wire harness assembly 2136 is pulled during installation or regular use. The nugget 2020 may include non-conductive and/or electrically insulating materials. Additionally, the nugget 2020 may include plastic over-molded material.

As shown, a grommet 2024 may be positioned adjacent the nugget 2020. The grommet 2024 may have a hollow tubular cross-section, such that the wire harness assembly 2136 may pass through the grommet 2024 and be coupled to the terminals 2018. The grommet 2024 may include a flexible and resilient material, such as a molded high temperature rubber.

The soot sensor assembly 2000 further includes an outer housing member 2026 having a first end 2028 and a second 2030 and a longitudinally disposed passageway 2032 extending from the first end 2028 to the second end 2030. The passageway 2032 is shaped and/or sized to receive and enclose the first and second spacing members 2014, 2016, the terminals 2018 and respective connections with lead wires from the sensor 1300 (shown in FIGS. 22A-22B), the nugget 2020, and a portion of the grommet 2024 within. The outer housing member 2026 may include one or more materials capable of inhibiting electrical communication and providing structural integrity and/or physical protection to components therein. The outer housing member 2026 may also include material capable of withstanding high temperatures.

In the illustrated embodiment, the second end 230 of the outer housing member 2026 defines a flange portion 2034. The flange portion 2034 is configured to engagingly mate with the flange portion 2012 of the second end 2008 of the inner housing member 2004. As such, the outer housing member 2026 may be coupled to at least the inner housing member 2004 at the respective flange portions 2034, 2012, wherein the flange portions 2034, 2012 may be sealed to one another by any known methods to provide a generally tight seal, thereby preventing moisture and/or other contaminants from entering the passageway 2032 of the outer housing member 2026 via the second end 2030.

When the outer housing member 2026 is positioned (e.g. slid) over components of the assembly 2000, a portion of the outer housing member 2026 at or near first end 2028 may be crimped, such that a diameter of the outer housing member 2026 may be reduced at or near the first end 2028. The crimped portion 2138 may compress a portion of the grommet 2024 positioned within the passageway 2032, wherein the compressed portion of the grommet 2024 may provide a generally tight seal and prevent moisture and/or other contaminants from entering the first end 2028 of the outer housing member 2026. The crimped portion 2138 may further securely retain and fix the nugget 2020 within the passageway 2032 of the outer housing member 2028.

FIG. 22A is a top sectional view of the soot sensor assembly of FIG. 21 taken along lines A-A and FIG. 22B is a side sectional view of the soot sensor assembly of FIG. 21 taken along lines B-B. As shown, a portion of the soot sensor 1300 is positioned and retained within the insulating member 2002. In the illustrated embodiment, lead wires 2240 coupled to the sensor 1300 (e.g. coupled to the first 1314, 1323 and second 1324, 1326 electrical contacts of the elements 1308, 1318) extend away from the sensor 1300 and into the passageway 2010 of the inner housing member 2004 and eventually into the passageway 2032 of the outer housing member 2026. The lead wires 2240 may be coupled to associated terminals 2018, as indicated by arrow 2242.

A portion of the lead wires 2240 may be secured in a relatively fixed position within the inner housing member 2004 by way of a fixing material 2244. In one embodiment, the fixing material 2244 may be disposed within a portion of the passageway 2010 of the inner housing member 2004 and completely surround a portion of the lead wires 2240. The fixing material 2244 may be provided in a liquid form and then cured. The fixing material 2244 may be configured to provide stability and vibration protection to the sensor 1300 and lead wires 2240, thereby improving thermal response. The fixing material 2244 may include non-conductive and/or electrically insulating material, as well as moisture and/or corrosive resistant material, such as thermosetting plastics.

In one embodiment, the fixing material 2244 may include glass and may be used to seal a portion of the lead wires 2240 and the sensor 1300 within a portion of the passageway 2010 of the inner housing member 2004, thereby increasing durability of the soot sensor 1300 and/or lead wires 2240 during production assembly and decreasing vibration tendency. As appreciated by one skilled in the art, a portion of the lead wires 2240 may be fixed and sealed within the inner housing member 2004 by other known methods, such as, for example, any known potting methods.

Turning to FIGS. 23A-23B, perspective and sectional views, respectively, of one embodiment of the inner housing member 2304 of the soot sensor assembly 2000 of FIG. 20 are generally illustrated. This embodiment is similar to the embodiment of FIG. 20, and like components have been assigned like reference numerals in the twenty-three hundreds rather than the two thousands. Generally, the inner housing member 2304 includes a first end 2306 and a second end 2308 and a longitudinally disposed passageway 2310 extending from the first end 2306 to the second end 2308. The second end 2308 defines a flange member 2312 configured to matingly engage a flange portion 1820 of the sensor tip 1812. The inner housing member 2304 further includes an expanded portion 2314 defined along a radius of the inner housing member 2304. As shown in FIG. 23B, the expanded portion 2314 results in a complementary recessed portion 2316 formed on an inner surface 2318 of the passageway 2310.

As previously described, a fixation material 2244, such as glass, for example, may be filled within a portion of the passageway 2310 to securely fix one or more lead wires 2240 within. The fixing material 2244 may fill the recessed portion 2316 within the passageway 2310. When the fixing material 2244 has cured, the recessed portion 2316 may provide a means of securing the cured fixing material 2244 within the passageway 2310. More specifically, the cured portion of the fixing material 2244 within the recessed portion 2316 will prevent substantial movement of the cured fixing material 2244 in at least a longitudinal direction (i.e. from the first to the second ends 2306, 2308 of the inner housing member 2304). Additionally, the interior surface 2318 of the passageway 2310 may be configured to improve interaction between the fixation material 2244 and the inner housing member 2304. For example, in one embodiment, the interior surface 2318 may be roughened by any know means (e.g., but not limited to, oxidized, etc.) so as to provide an improved interaction between the fixation material 2244 and the interior surface 2318.

FIGS. 24A-24B are perspective and sectional views, respectively, of another embodiment of the inner housing member 2404 of the soot sensor assembly 2000 of FIG. 20. Generally, the inner housing member 2404 includes a first end 2406 and a second end 2408 and a longitudinally disposed passageway 2410 extending from the first end 2406 to the second end 2408. The second end 2408 defines a flange member 2412 configured to matingly engage a flange portion 1820 of the sensor tip 1812. The inner housing member 2404 further includes a recessed portion 2414 defined along a radius of the inner housing member 2404. As shown in FIG. 24B, the recessed portion 2314 generally results in a complementary generally annular ridge portion 2416 extending from an inner surface 2418 towards a center of the passageway 2410.

When the fixing material 2244 is filled within the passageway 2410, the fixing material 2244 may engage and fill around the ridge portion 2416 within the passageway 2410. When the fixing material 2244 has cured, the ridge portion 2416 may prevent movement of the cured fixing material 2244, thereby securing the cured fixing material 2244 within the passageway 2410. Similar to the embodiment of FIGS. 23A-23B, the interior surface 2418 of the passageway 2410 may be configured to improve interaction between the fixation material 2244 and the inner housing member 2404. For example, in one embodiment, the interior surface 2418 may be roughened by any know means (e.g., but not limited to, oxidized, etc.) so as to provide an improved interaction between the fixation material 2244 and the interior surface 2418.

Figure 25:
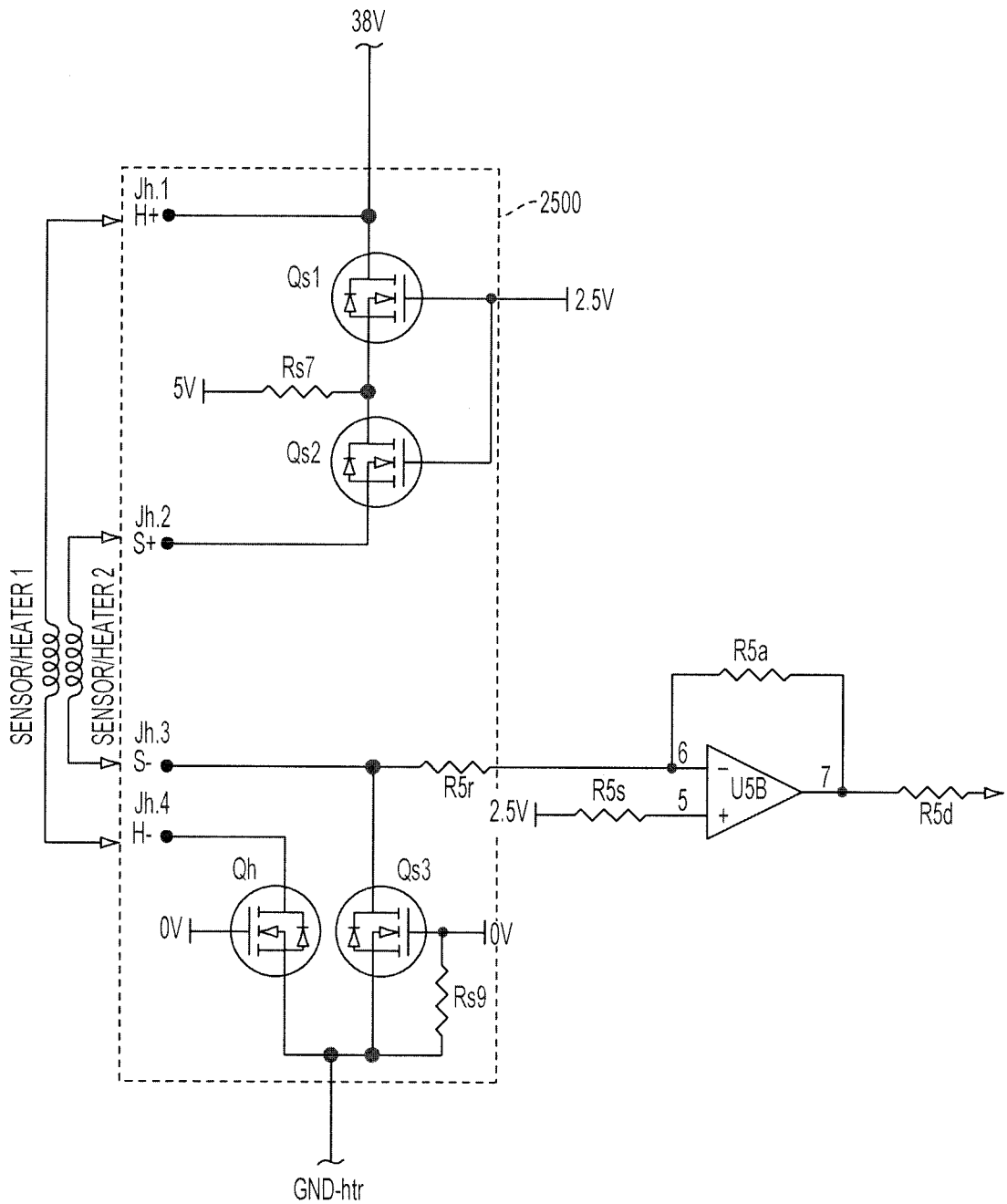
FIG. 25 is a schematic view of circuitry coupled to the soot sensor of FIG. 13.

FIG. 25 is a schematic view of circuitry coupled to the soot sensor of FIG. 13. The circuitry of FIG. 25 provides a means of nullifying leakage current effects when attempting to enhance soot collection of the soot sensor 1300. As shown, the first and second sensor/heater elements (e.g. Sensor/Heater1 and Sensor/Heater 2) may be configured for coupling to circuitry 2500 for providing current through the conductive materials of the first and second sensor/heater elements, wherein the current may be provided by a power supply configured to supply an input voltage, for example, of 38 V. In the illustrated embodiment, the circuitry 2500 may include a first transistor Qs1, a second transistor Qs2, a third transistor Qs3, and a fourth transistor Qs4. The transistors Qs1-Qs4 may include any type of switching device. In the illustrated embodiment, the transistors Qs1-Qs4 may include MOSFETs. The transistors Qs1-Qs4 may be configured to control the application of current from the power supply to the first and/or second heater elements.

As shown, Qh is off and the third transistor Qs3 is off, thereby providing the same potential (0V) at the source as the gate through resistor Rs9. A voltage of 2.5V is applied to the first and second transistors Qs1, Qs2, thereby resulting in both the first and second transistor Qs1, Qs2 being off. When the first transistor Qs1 off, an voltage of 5V will be applied to the drain of the second transistor Qs2 through the pull-up resistor Rs7. A 2.5V potential is thereby provided at the drain of the third transistor Qs3 and the source of the second transistor Qs2 through resistor R5r. With the circuit arranged as described, the second transistor Qs2 will have a 5V potential at its drain and 2.5V at its source, resulting in a drain-source voltage drop of 2.5V. Additionally, with 2.5V at the source and 2.5V at the gate of the second transistor Qs2, the second transistor Qs2 will have a 0V difference in potential between its gate and its source. The third transistor Qs3 will have a 2.5V potential at its drain, and with its source being grounded, a potential of 0V at its source, resulting in a drain-source voltage drop of 2.5V, matching that of the second transistor Qs2. With the gate and source of the second transistor Qs2 being at the same potential as that of the third transistor Qs3, the resulting difference in potential between the third transistors Qs3 gate and source is 0V, again, matching that of the second transistor Qs2. With both the second and third transistors Qs2, Qs3 equally biased, the soot measurement can be taken with the leakage current effects being cancelled out.

Figure 26:
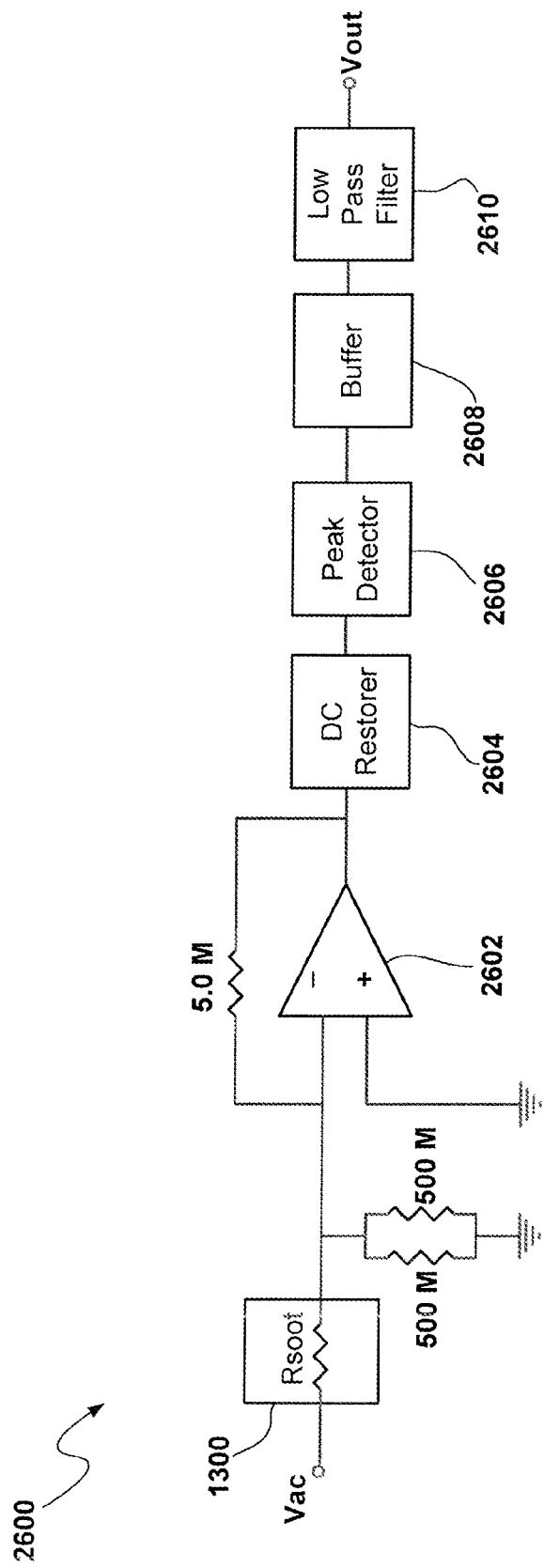
FIG. 26 is a block diagram of a signal processing system coupled to the soot sensor of FIG. 13.

FIG. 26 is a block diagram of an alternating current (AC) coupled signal processing system coupled to the soot sensor of FIG. 13. The AC coupled signal processing system 2600 may include the soot sensor 1300, as shown in FIG. 13, configured to receive an input AC supply voltage Vac and coupled to an amplifier 2602 configured to receive signal currents passing through the soot sensor 1300, including the resistance between the first and second sensor/heater elements 1308, 1318 (Rsoot). The system 2600 may further include a DC restorer 2604 coupled to the amplifier 2602. The DC restorer 2604 may be configured to synchronously ground signals from said amplifier 2602. A peak detector 2606 may be coupled to and configured to receive signals from the DC restorer 2604. Additionally, a buffer 2608, such as a unity gain operational amplifier (shown in FIG. 20), may be coupled to and configured to receive signals from the peak detector 2606. The system 2600 may further include a low pass filter 2610 coupled to and configured to receive signals from the buffer 2608, wherein the low pass filter 2610 may be configured to remove switching transients from received. With the assumption of a dynamic resistance of 500 M Ohms to both ground and to the input power supply, the AC equivalent circuit is illustrated as two 500 M Ohm resistors to ground. Additionally, incrementally, the two 500 M Ohm resistors are coupled between ground and the inverting input of the operational amplifier 2602, and, as such, may have little effect on an AC signal (current).

Figure 27:
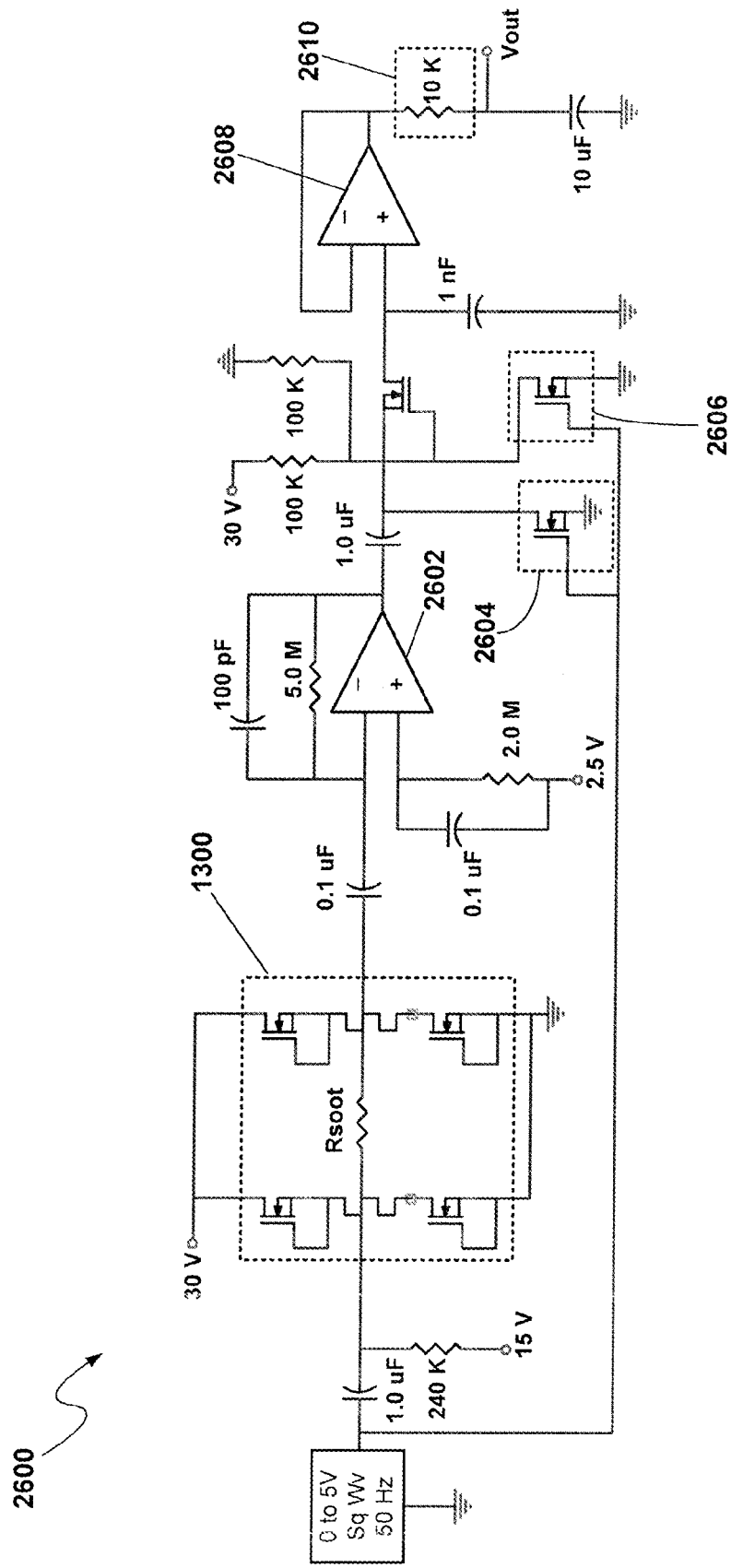
FIG. 27 is a schematic view of the signal protection circuitry of FIG. 26.

FIG. 27 is a schematic view of the circuitry of the signal processing system of FIG. 26. To lessen the effect of the DC leakage currents that may occur in transistors of the circuitry of the soot sensor 1300, an AC coupled approach can be implemented. Due to the fact that the dynamic resistance of the DC leakage of the transistors may be much larger than the DC resistance, an AC voltage divider would take advantage of this effect. The dynamic resistance of an ideal constant current source is ∞ Ohms. The dynamic resistance of the leakage of the transistors is δv/δi. In one example, the dynamic resistance may be approximately 500 M Ohms. This value may be more stable with changes in leakage and operating point.

By utilization of the AC coupled signal processing system 2600, the DC leakages of the transistors can be effectively eliminated from the resistance measurement Rsoot. The system 2600 may take advantage of very high dynamic resistance of the sources of leakage currents. For example, the system 2600 takes advantage of being able to couple the square wave stimulation and the resultant AC signals via capacitors, thereby allowing a desired AC signal to pass through the circuitry unattenuated (with properly sized capacitors). The undesired DC voltages (due to leakage currents of the transistors) and/or slow varying voltages due to thermal effects, may be rejected.

Referring to FIG. 27, the soot sensor 1300 may be configured to receive a variety of signal frequencies having varying waveforms (square, saw tooth, sinusoidal, etc) depending on the application taking into account any software and/or firmware and/or hardware included in the system and/or sensor. In the illustrated embodiment, the soot sensor 1300 may be configured to receive a signal having a square waveform having frequency of 50 Hz. It should be noted that the optimum frequency may help add robustness to EMC, allow better integration with the software and firmware as well as the hardware and might also have effects of signal to noise ratio and perhaps add to stability over life.

Additionally, the wave may be balanced around zero volts, such that the wave may cycle equally plus and minus relative to ground. Additionally, a standard waveform may be used that cycles from ground to some predetermined voltage level, such as 30 Vdc, resulting in a non-balanced waveform. The non-balanced version may decrease the life of Pt electrodes due to migration of the Pt. However, the non-balanced may be cheaper to implement as far as costs are concerned.

The AC coupled signal processing system 2600 may be configured to effectively eliminate DC leakages from transistors in the soot sensor circuitry. During operation, the DC restorer 2604 may be configured to synchronously ground the signal during the low voltage side of the square wave, thereby producing a zero voltage based square wave on the output side of the 1.0 uF capacitor. Additionally, the series connected MOSFET synchronously passes the peak value of this square wave to the 1.0 nF capacitor. This capacitor holds this peak value until the next cycle. This voltage is buffered by a unity gain op-amp 2608 and the output is then low pass filtered via the low pass filter 2610 to remove switching transients. In one example, in which there is no current leakage, if Rsoot is 100 M, then Vout is 5V*5.0 μA/(3.0 μA+100M)=0.24 V. Similarly, if Rsoot is 5 M, then Vout is 5V*5.0 ΞA/(5.0 μA+5.0M)=2.5 V.

Figure 28:
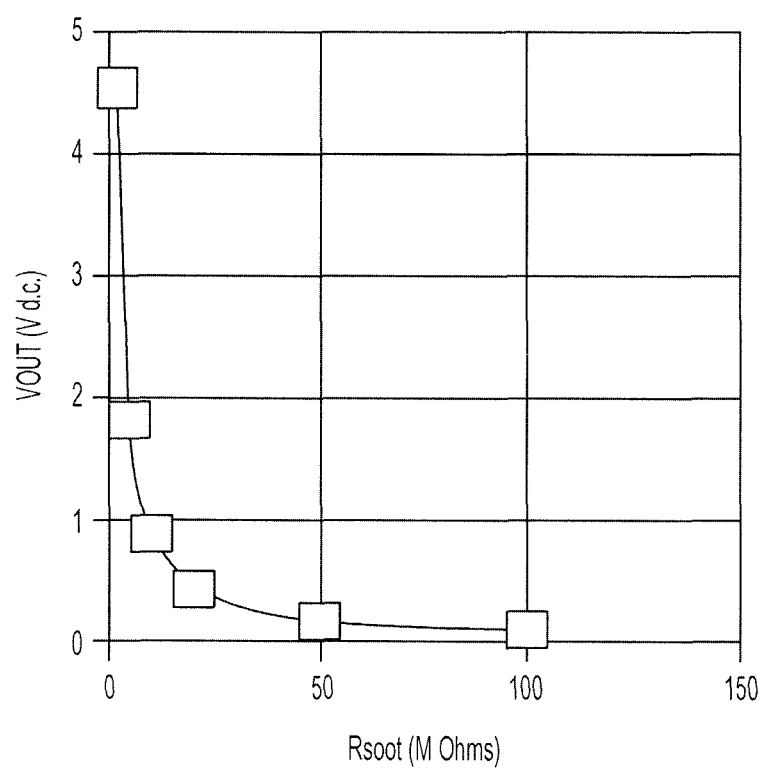
FIG. 28 is a plot of output voltage vs. resistance associated with an exemplary soot sensor consistent with the present disclosure.

FIG. 28 is a plot of output voltage vs. resistance associated with an exemplary soot sensor consistent with the present disclosure. The following table (shown immediately below) includes the measurements of the resistance Rsoot between the two heater elements during a soot measurement cycle and the corresponding output voltage Vout at 25° C. and 105° C.

| Rsoot (M Ohms) | Vout (V) at 25° C. | Vout (V) at 105° C. |
| --- | --- | --- |
| 2 | 4.55 | 4.55 |
| 5 | 1.84 | 1.83 |
| 10 | 0.88 | 0.88 |
| 20 | 0.44 | 0.44 |
| 50 | 0.18 | 0.18 |
| 100 | 0.09 | 0.09 |

In the illustrated embodiment, because of the design of the circuitry of the AC coupled signal processing system 2600, the output voltage Vout is proportional to 1/Rsoot. This data exhibits a high degree of temperature stability. The 1/Rsoot method gives high resolution at the lower values of Rsoot, where it is desired.

Figure 29:
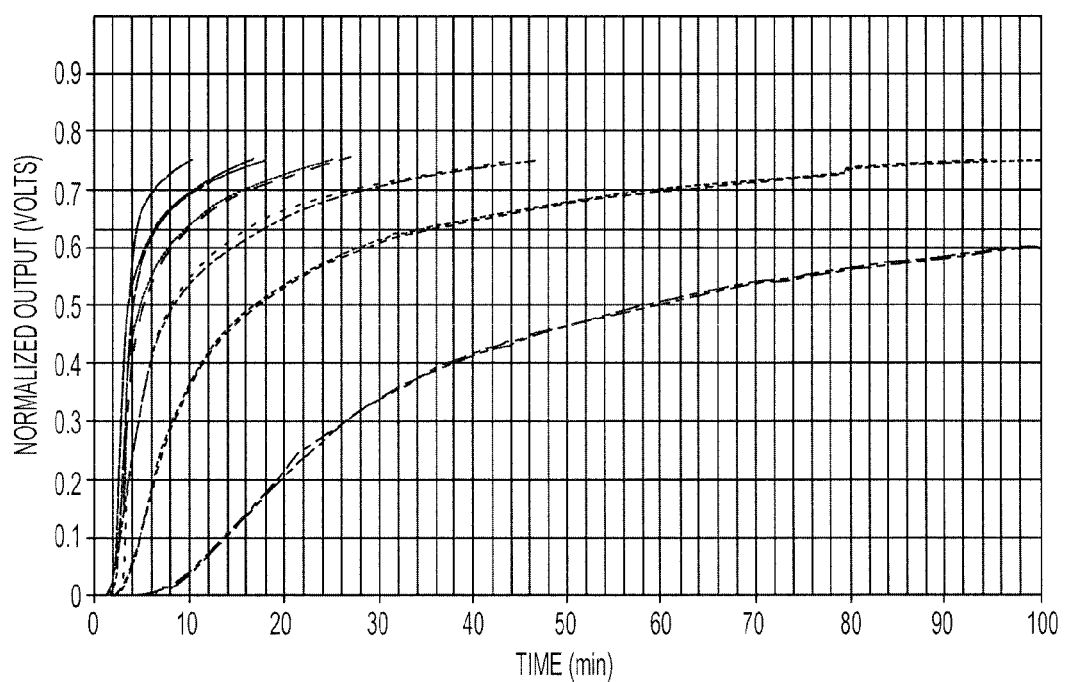
FIG. 29 includes plots of output voltage vs. time associated with an exemplary soot sensor consistent with the present disclosure.

FIG. 29 includes plots of output voltage vs. time associated with an exemplary soot sensor consistent with the present disclosure. The voltage (peak to peak) signal used to measure the resistance Rsoot may affect the sensor response time. As voltage is increased, response time is decreased. Since the circuit of the AC coupled signal processing system may be configured to operate on a 5 Vdc supply, a charge pump or other means may implemented, thereby increasing sensor excitation voltage. This may result in the required current from the 5 Vdc supply to increase.

Figure 30A:
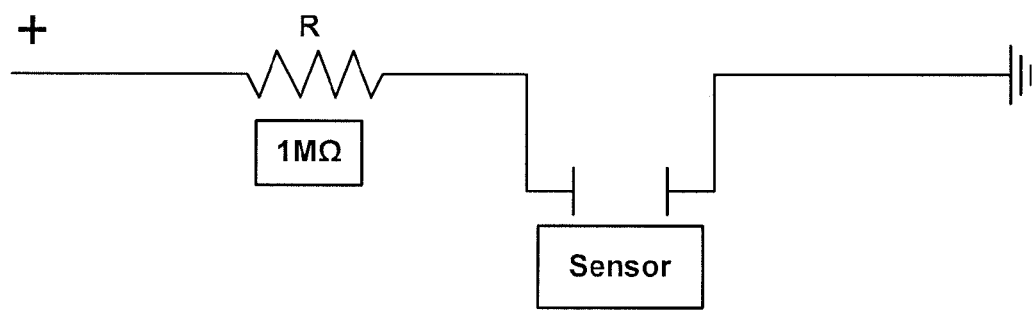
FIG. 30A is a schematic view of circuitry associated with an exemplary soot sensor consistent with the present disclosure.
Figure 30B:
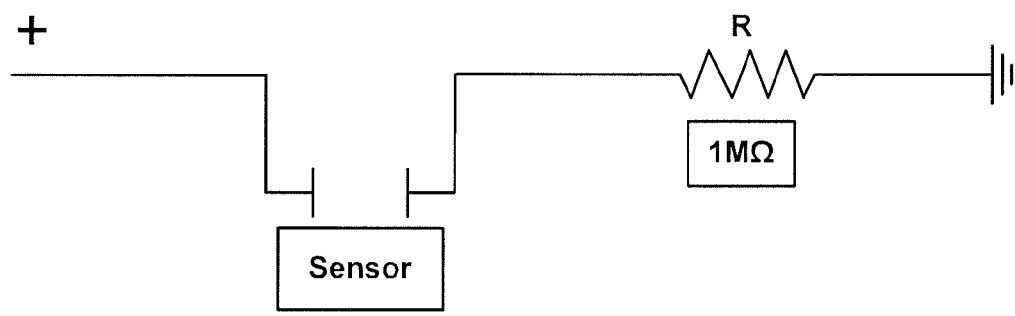
FIG. 30B is a schematic view of circuitry associated with an exemplary soot sensor consistent with the present disclosure.

FIGS. 30A and 30B are schematic views of circuitry associated with an exemplary soot sensor consistent with the present disclosure. FIG. 30A depicts a pull up resistor configuration and FIG. 30B depicts a pull down resistor configuration.

Figure 31:
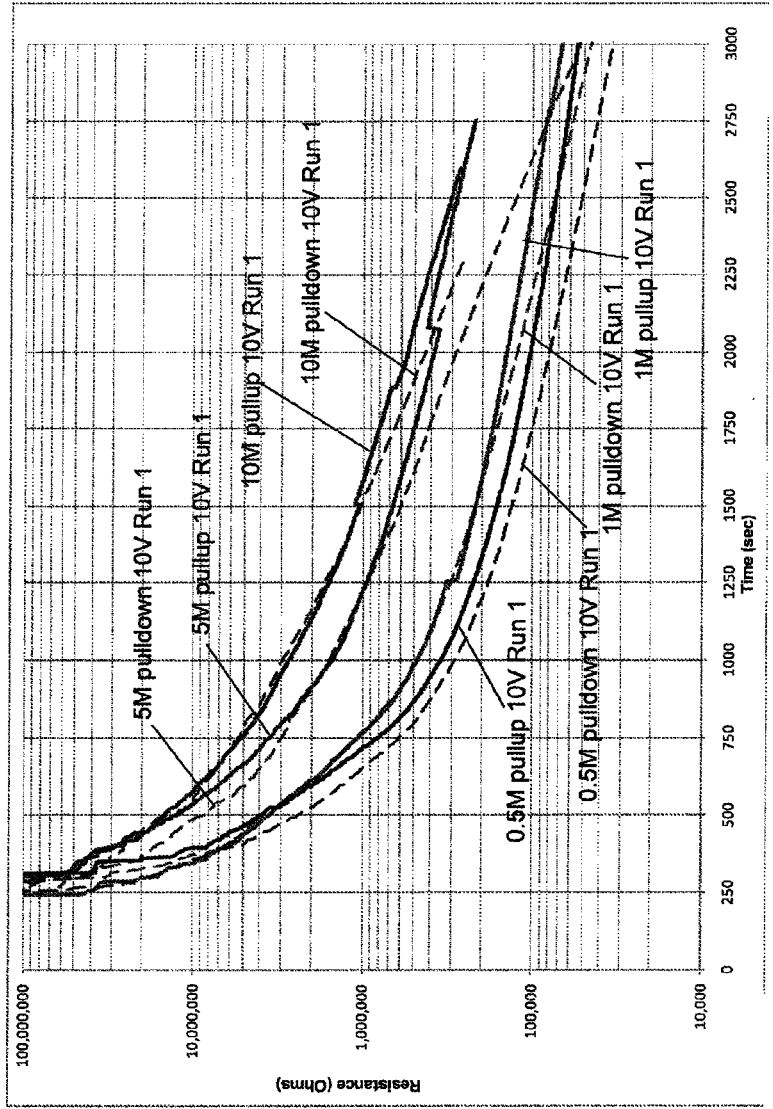
FIG. 31 is a plot of resistance vs. time associated with the circuitry of FIGS. 30A-30B.

FIG. 31 includes plots of resistance vs. time associated with the pull up and pull down resistor configurations of FIGS. 30A-30B. FIG. 31 illustrates the resistance of the pull up and pull down resistor configurations at two separate excitations voltages, including 10V and 5V. In the illustrated embodiment, the pull down resistor configuration created a slightly improved sensor response with smoother output signals.

Figure 32:
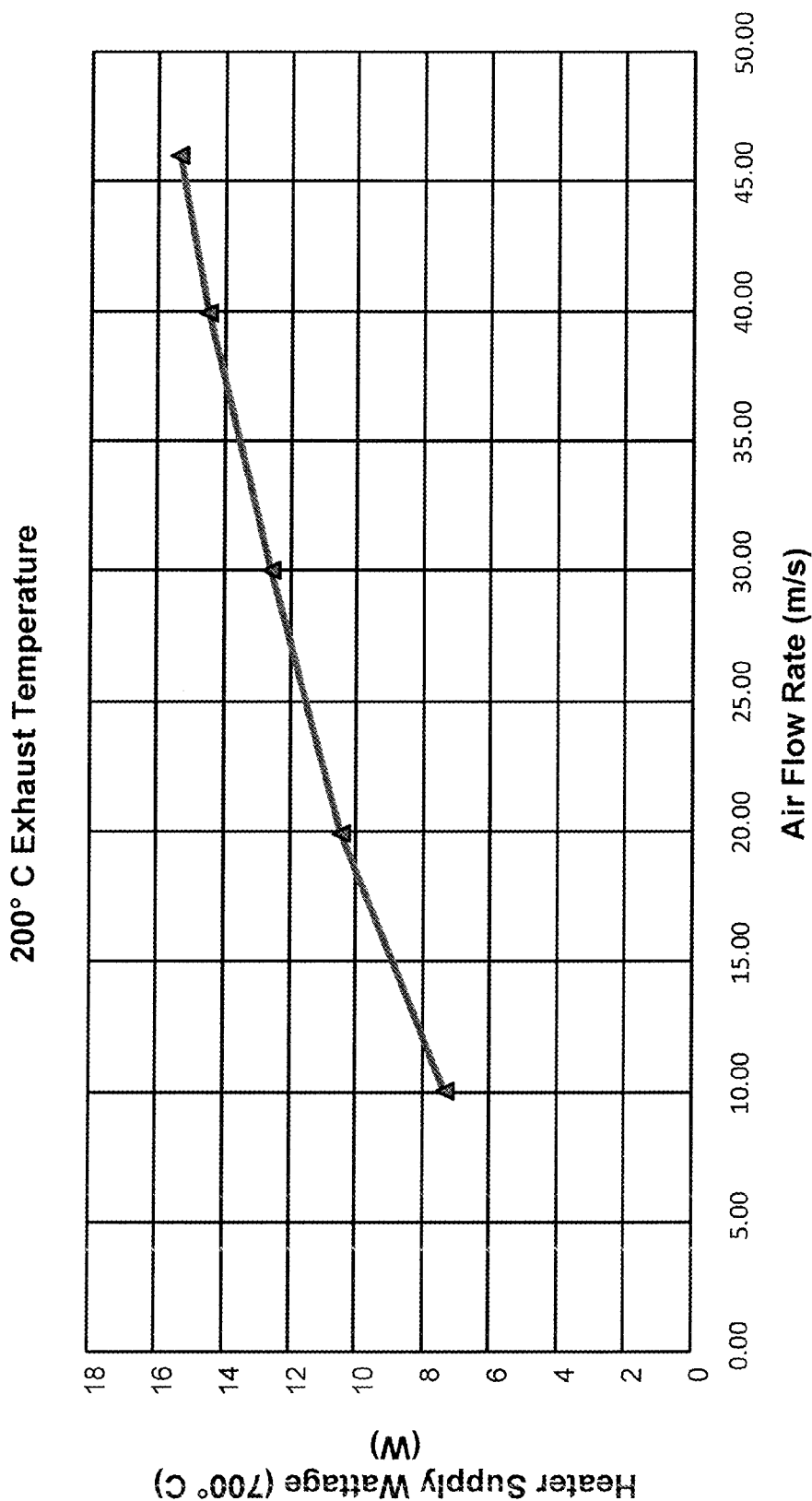
FIG. 32 is a plot of supply wattage vs. air flow rate associated with an exemplary soot sensor consistent with the present disclosure.
Figure 33A:
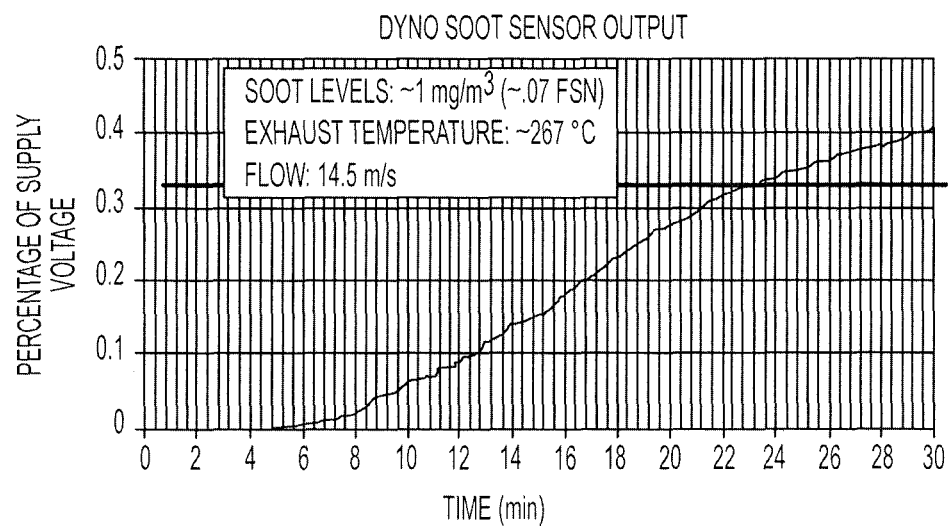
FIGS. 33A-33D are plots of supply voltage vs. time associated with an exemplary soot sensor consistent with the present disclosure.
Figure 33B:
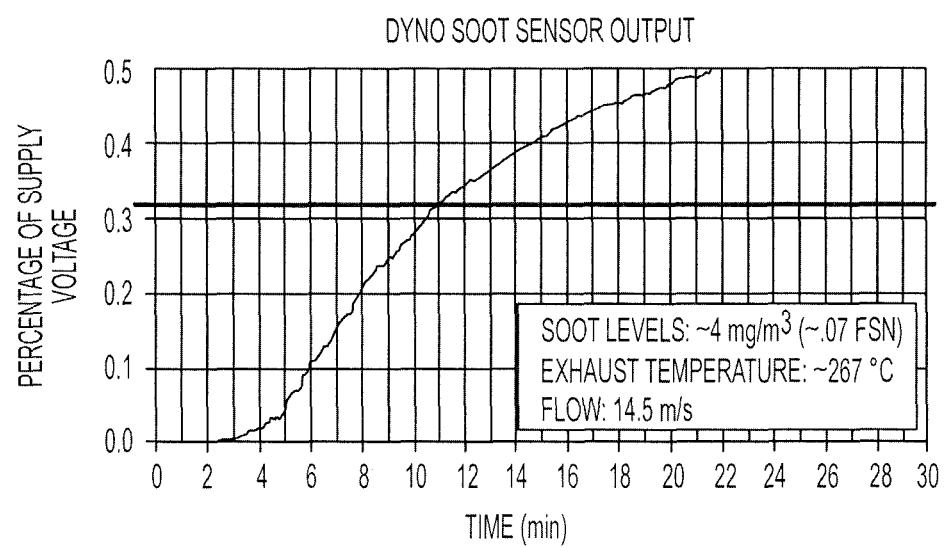
Figure 33C:
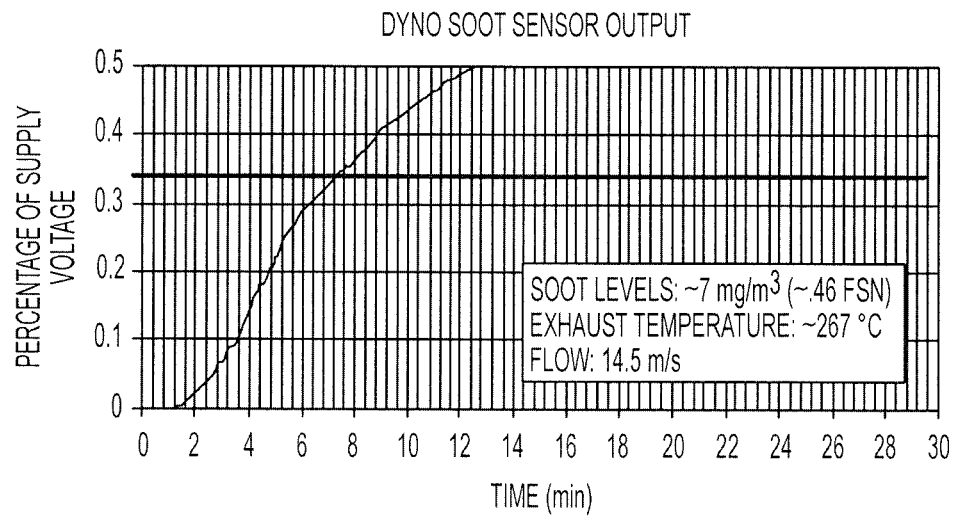
Figure 33D:
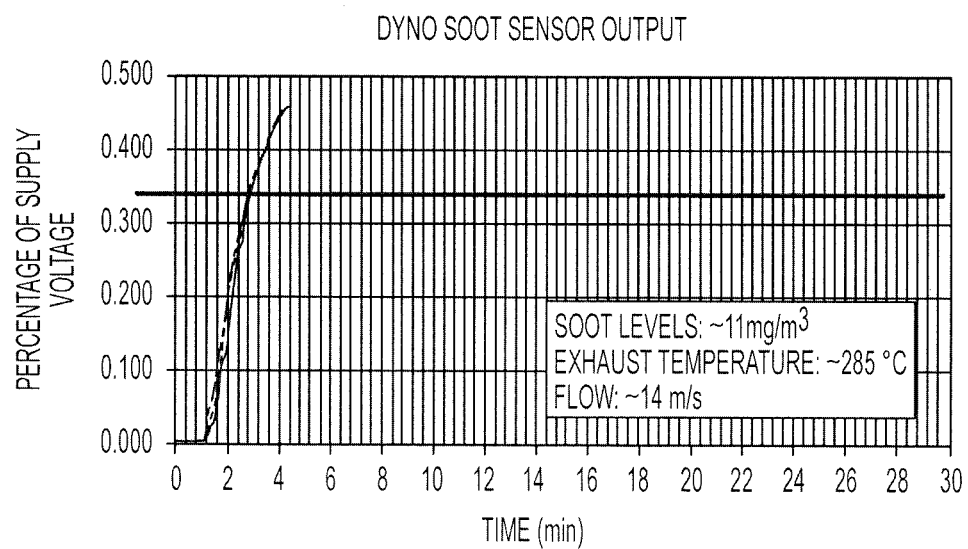

FIG. 32 is a plot of supply wattage vs. air flow rate associated with an exemplary soot sensor consistent with the present disclosure exposed to an exhaust gas having a temperature of 200° C. Embodiments of a soot sensor described herein may be configured to operate in a temperature range of 0° C. to 650° C., with excursions to 950° C. For example, a soot sensor consistent with the present disclosure may be configured to operate in an exhaust gas temperate ranging from 150° C. to 650° C. The wattage required to get the sensor to its regeneration temperature varies with exhaust temperature and flow velocity. The wattage is predictable and repeatable for these different conditions. In the illustrated embodiment, the x-axis illustrates different exhaust velocities and the y-axis illustrates the required wattage for the sensor to reach its regeneration temperature. The wattage is calculated by measuring voltage across the first and second heater elements, as well as any current passing the first and second heater elements. Knowing voltage and current also allows resistance of the heater to be calculated. The resistance vs. temperature curve of the heater is also known. By monitoring the resistance of the heater at regeneration temperature, it can be determined if the heater resistance has changed or drifted out of its acceptable window.

When the soot sensor is exposed to an exhaust gas stream, certain materials present in the exhaust gas may not be completely incinerated by the heater elements during sensor regeneration. These materials may include ash and/or iron oxide, for example. These materials may build up on the surface of the sensor over time and cause a shift in the response curve of the sensor (Response curve: the change in sensor resistance vs. mg of soot present on the sensor face). Schemes may be implemented to counteract the effect of these materials over time. For example, after dew point is reached, the sensor could be taken through a regeneration cycle and the sensor may store a current resistance in the soot free state. If this resistance is different than previously seen then the offset could be used to compensate for the expected sensor response curve.

In one aspect, the present disclosure may feature a method of predicting soot concentration on a soot sensor. The method may include measuring the time between sensor regenerations and determining the average soot concentration during that time frame. The time between regenerations can be less than a couple minutes to over 20 minutes with typical soot concentration levels. However, with very low soot concentration levels, the time between regeneration cycles can be much longer. The main disadvantage to this method is that it only provides the average soot concentration level over a fairly long time period making it slow, especially at low soot concentration levels.

In another aspect, the present disclosure may feature a method of predicting soot concentration on a soot sensor. This method may be faster in soot concentration determination than the previous method described above. The actual response of the sensor (change in sensor resistance vs. time) is used to calculate the mass of soot that is present on the sensor in smaller slices of time "real time". This method uses the change in resistance vs. time or as measured in change in voltage vs. time.

FIGS. 33A-33D are plots of supply voltage vs. time associated with an exemplary soot sensor consistent with the present disclosure. The curves illustrated in FIGS. 33A-33D are shown with exhaust flow at 15 m/s and exhaust temperature at 270° C. The x-axis is in minutes and the y-axis is percentage of supply voltage. The soot sensor used in each of the curves is coupled to a pull down resistor (shown in FIG. 30B) on the low side. The voltage measurement (output signal) is measured across the pull down resistor. As can most clearly be seen in FIGS. 33A-33D, as soot concentration increases, the slope of the sensors also increases. The horizontal blue line indicates the percentage of supply voltage at which the sensor gets regenerated. The blue line shown was picked to allow the sensor response to be measured primarily in the linear region of the sensor response slope. It is possible to further shorten the time span between sensor regenerations, such as 10% in static states. If the soot concentration is changing a lot (known by slope changes in the sensor curve) then other percentages could be used. This would result in less soot on the sensor allowing regeneration to occur more quickly.

Figure 34:
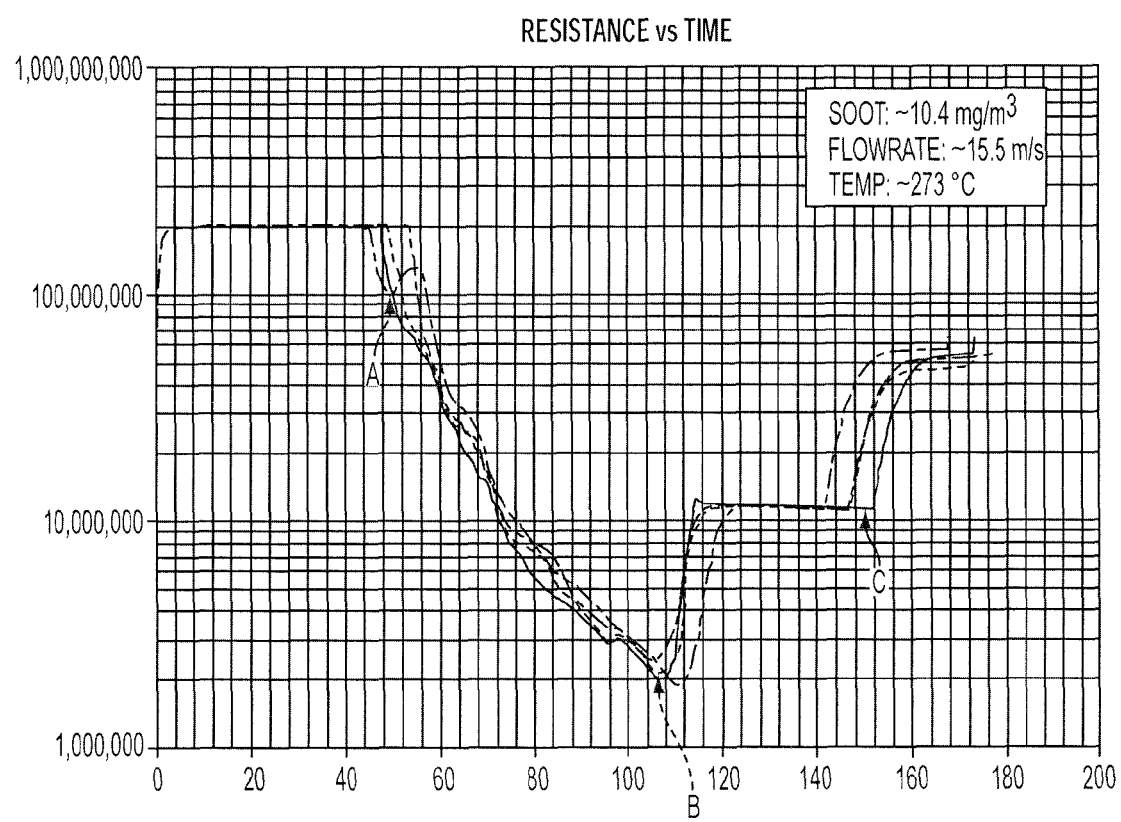
FIG. 34 is a plot of resistance vs. time associated with an exemplary soot sensor consistent with the present disclosure.

FIG. 34 is a plot of resistance vs. time associated with an exemplary soot sensor consistent with the present disclosure. The soot sensor was exposed to an exhaust gas having a known soot concentration of approximately 10.4 mg/m³, a flow rate of approximately 15.5 m/s and a temperature of approximately 273° C. The resistance of the soot sensor was measured through a full cycle (e.g. sensing of soot accumulation through full regeneration of soot sensor). As indicated by arrow A, the sensor resistance begins to drop with soot accumulation. Once a predetermined threshold resistance is reached, as indicated by arrow B, the sensor switches from a soot sense mode to a regeneration mode. As the soot is cleaned from the soot sensor, the resistance begins to increase. As indicated by arrow C, the regeneration mode has ended.

Figure 35:
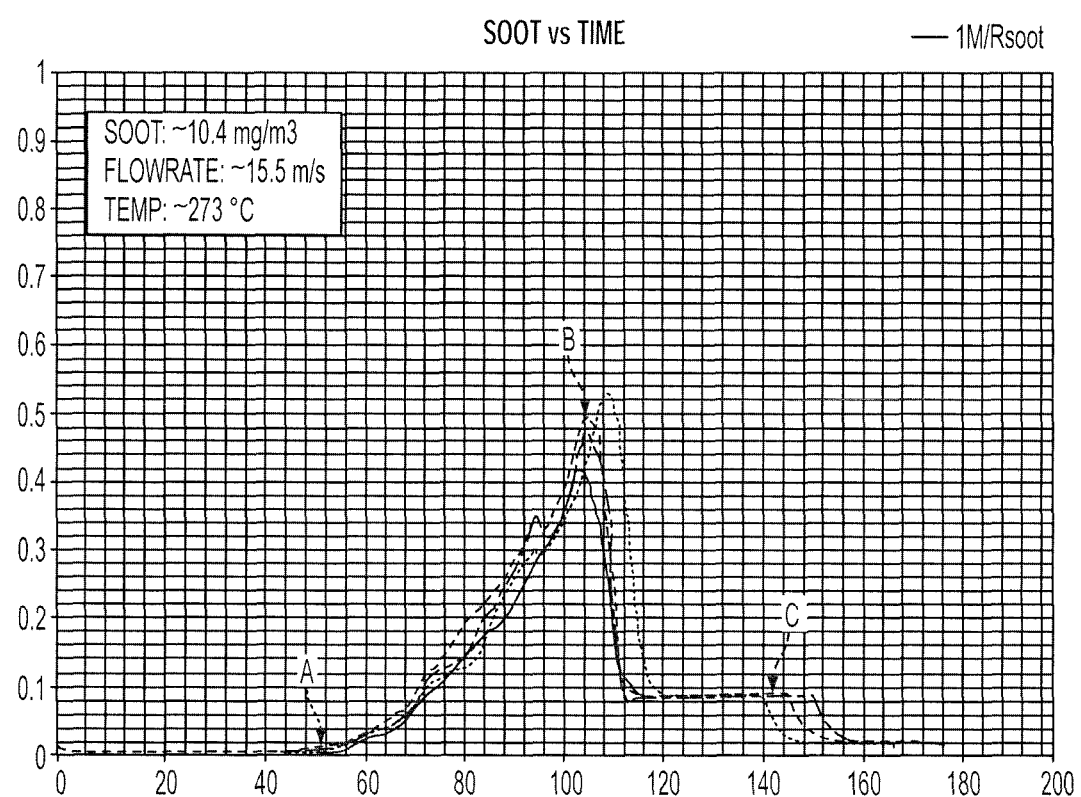
FIG. 35 is a plot of soot accumulation vs. time correlating to the plot of FIG. 34.

FIG. 35 is a plot of soot accumulation vs. time correlating to the plot of FIG. 34. Generally, FIG. 35 is a linearization of the measurement of resistance vs. time of FIG. 34. As shown, soot begins to accumulate at approximately the same time the resistance begins to drop (shown in FIG. 34). Similarly, the moment the soot accumulates and reaches a predetermined threshold, as indicated by arrow B, the regeneration mode begins and the soot accumulation level begins to drop (coinciding with the increase in resistance of FIG. 34). Linearization of the plot of resistance vs. time into soot accumulation vs. time was determined using the formula equation Sensor V out=$9206/\sqrt{R}$, where Sensor V out is the output voltage of the sensor and R is resistance. It should be noted that this is an exemplary formula equation and other equations may be used for the linearization of the plot of FIG. 34.

Figure 36:
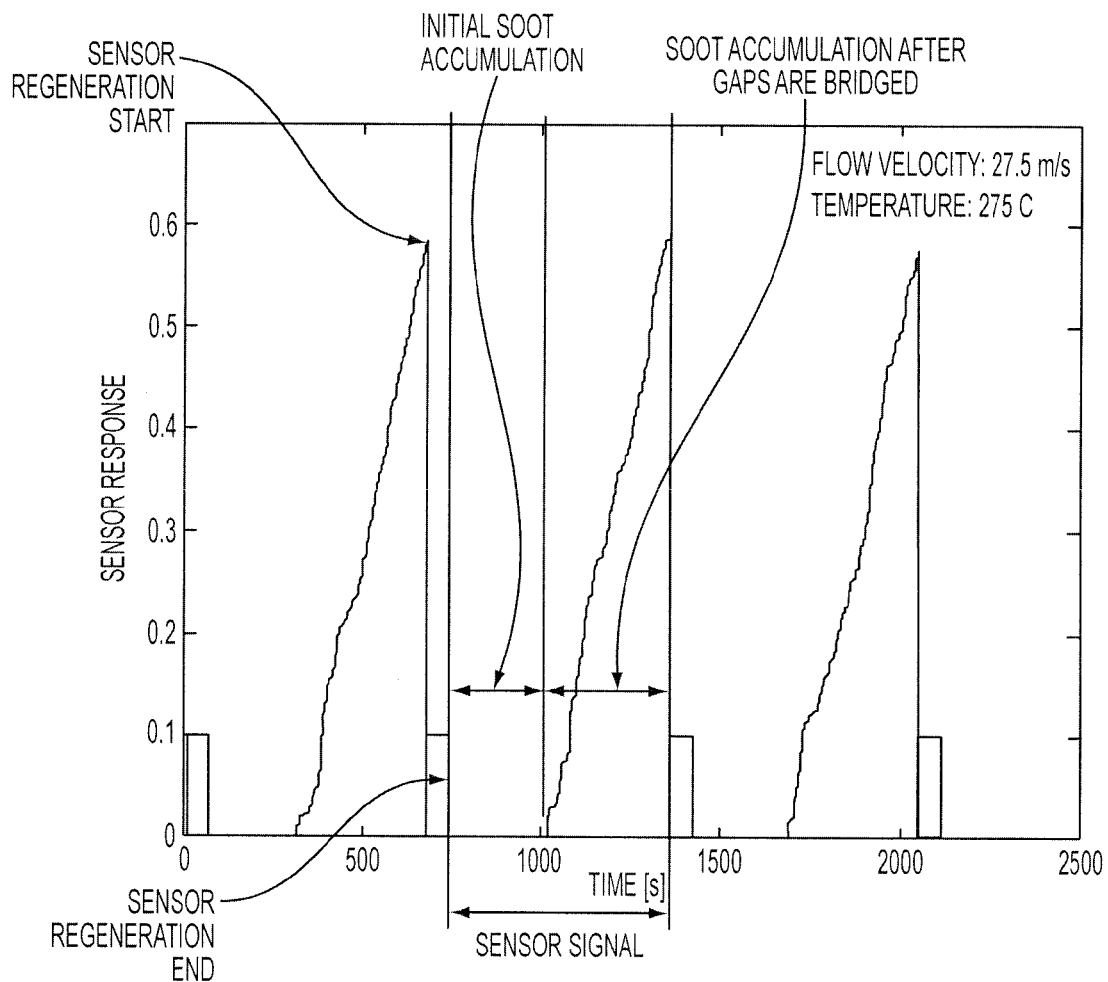
FIG. 36 is a plot of sensor response vs. time associated with an exemplary soot sensor consistent with the present disclosure.

FIG. 36 is a plot of sensor response vs. time associated with an exemplary soot sensor consistent with the present disclosure. The soot sensor was exposed to an exhaust gas having a flow rate of approximately 27.5 m/s and a temperature of approximately 275° C.

A soot sensor consistent with the present disclosure provide numerous advantages. The single-layer design of the first and second sensor/heater elements 1308, 1318 of the soot sensor 1300 of FIG. 13, for example, provides numerous unique and advantageous features. For example, the effectiveness of regeneration of the soot sensor is improved due to the fact that elements may have the ability to both sense soot accumulation and to heat up to regenerate (i.e. clean) the substrate surface. As such, the elements may serve both roles and there is no need to heat a separate surface, such as the second opposing surface (e.g. back) of the substrate. Additionally, regeneration in high flow conditions is improved. The second surface (e.g. back) of the substrate may be available for additional components, such as another sensor (e.g. high precision exhaust gas temp sensor, etc.) which further adds value and versatility to a system and may reduce costs.

The single layer design also uses less materials, including, but not limited to, platinum, when compared to some currently known resistive PM sensors. The price of precious metals is relatively high and may continue to escalate as it is a finite supply.

A soot sensor circuitry consistent with the present disclosure also provides immediate sensor diagnostics self check upon key and on during cold start without operating in regeneration mode. The circuitry is relatively simple and reliable and a diagnostics check may be performed using low current loop.

Consistent with one embodiment of the present disclosure, there is provided a soot sensor. The soot sensor includes a substrate defining a first surface and a second surface opposing the first surface. The soot sensor further includes a first element having at least one continuous loop of conductive material disposed on the first surface of the substrate. The at least one element is configured to operate in a first mode to sense accumulation of soot on at least the first surface of the substrate and to operate in a second mode to remove accumulated soot on at least the first surface of the substrate.

Consistent with another embodiment of the present disclosure, there is provided a soot sensor system. The soot sensor system includes a soot sensor. The soot sensor includes a substrate defining a first surface and a second surface opposing the first surface. The soot sensor further includes a first element having at least one continuous loop of conductive material disposed on the first surface of the substrate. The at least one element is configured to operate in a first mode to sense accumulation of soot on at least the first surface of the substrate and to operate in a second mode to remove accumulated soot on at least the first surface of the substrate.

The soot sensor system further includes circuitry electrically coupled to the first element. The circuitry is configured to provide electrical current to the first element and to determine an amount of soot accumulated on the first surface of the substrate and the first element and to control heating of first element in response to the soot accumulated on the first surface of the substrate and the first element.

Consistent with yet another embodiment of the present disclosure, there is provided a method of measuring an amount of soot deposited on a soot sensor. The method includes providing a soot sensor. The soot sensor includes a substrate defining a first surface and a second surface opposing the first surface. The soot sensor further includes a first element having at least one continuous loop of conductive material disposed on the first surface of the substrate. The at least one element is configured to operate in a first mode to sense accumulation of soot on at least the first surface of the substrate and to operate in a second mode to remove accumulated soot on at least the first surface of the substrate.

The method further includes monitoring a sense current through the first element, the current being representative of an amount of soot accumulated on the first element. The method further includes providing heater current through the first element in response to the monitoring step when the sense current reaches a predetermined threshold to thereby remove at least a portion of the soot accumulated on the first element.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

What is claimed is:

1. A soot sensor comprising:
    a substrate defining a first surface and a second surface opposing said first surface;
    a first element having at least one continuous loop of conductive material disposed on said first surface of said substrate, said first element being configured to operate in a first mode to sense accumulation of soot on said first surface of said substrate and to operate in a second mode to remove accumulated soot on said first surface of said substrate;
    a second element having at least one continuous loop of conductive material disposed on said first surface of said substrate, said second element being configured to operate in a first mode to sense accumulation of soot on said first surface of said substrate and to operate in a second mode to remove accumulated soot on said first surface of said substrate; and
    a tip configured to at least partially enclose said soot sensor, said tip comprising a body having an exterior surface and an interior surface, said body defining at least one channel defining a path from said exterior surface of said body to said interior surface of said body, said path configured to direct exhaust gas flow to said soot sensor.

2. The soot sensor of claim 1, wherein said first element is provided in a serpentine configuration comprising a first set of a plurality of undulations and a plurality of gaps defined between each of said plurality of undulations.

3. The soot sensor of claim 1, wherein said first element comprises first and second electrical contacts at opposite ends thereof.

4. The soot sensor of claim 3, wherein a resistance between said first and second electrical contacts changes as soot particles accumulate on said first element.

5. The soot sensor of claim 1, further comprising a protective layer formed over said first surface of said substrate and covering at least a portion of said first element, said protective layer configured to insulate at least a portion of said first element from exhaust gas flow.

6. The soot sensor of claim 5, wherein said first element is provided in a serpentine configuration comprising a first set of a plurality of undulations and a plurality of gaps defined between each of said plurality of undulations, and wherein said protective layer defines a plurality of channels corresponding to and aligned with said plurality of gaps of said first element, such that portions of said conductive material of said first element are exposed to exhaust gas flow and soot particles therefrom.

7. The soot sensor of claim 1, wherein said second element is provided in a serpentine configuration comprising a second set of a plurality of undulations interweaving with said first set of said plurality of undulations of said first element, and wherein said second element comprises first and second electrical contacts at opposite ends thereof.

8. The soot sensor of claim 7, further comprising a switch coupled between one of said first and second electrical contacts of said first element and one of said first and second electrical contacts of said second element, said switch being configure to connect said first element loop and said second element loop in series when said switch is closed.

9. A soot sensor system comprising:
    a soot sensor comprising:
        a substrate defining a first surface and a second surface opposing said first surface;
        a first element having at least one continuous loop of conductive material disposed on said first surface of said substrate, said first element being configured to operate in a first mode to sense accumulation of soot on said first surface of said substrate and to operate in a second mode to remove accumulated soot on said first surface of said substrate; and
        a second element having at least one continuous loop of conductive material disposed on said first surface of said substrate, said second element being configured to operate in a first mode to sense accumulation of soot on said first surface of said substrate and to operate in a second mode to remove accumulated soot on said first surface of said substrate; and
    circuitry electrically coupled to said first element, said circuitry configured to:
        cause a sense current to be applied to at least one of said first or said second element and to detect soot accumulated on said first surface of said substrate;
        cause a heater current to be applied to at least one of said first or said second element and to control heating of said soot sensor in response to said soot accumulated on said first surface of said substrate; and
        detect an open circuit of at least one of said first or said second elements based on a diagnostics sense current applied to said at least one of said first or said second elements.

10. The system of claim 9, wherein said first element is provided in a serpentine configuration comprising a first set of a plurality of undulations and a plurality of gaps defined between each of said plurality of undulations.

11. The system of claim 9, further comprising a protective layer formed over said first surface of said substrate and covering at least a portion of said first element, said protective layer configured to insulate at least a portion of said first element from exhaust gas flow.

12. The system of claim 9, wherein said first element comprises first and second electrical contacts at opposite ends thereof, wherein a resistance between said first and second electrical contacts changes as soot particles accumulate on said first element.

13. The system of claim 9, wherein said second element is provided in a serpentine configuration comprising a second set of a plurality of undulations interweaving with said first set of said plurality of undulations of said first element, and wherein said second element comprises first and second electrical contacts at opposite ends thereof.

14. The system of claim 13, said soot sensor further comprising a switch coupled between one of said first and second electrical contacts of said first element and one of said first and second electrical contacts of said second element, said switch being configure to connect said first element loop and said second element loop in series when said switch is closed.

15. The system of claim 9, further comprising a tip configured to at least partially enclose said soot sensor, said tip comprising a body having an exterior surface and an interior surface, said body defining at least one angularly disposed channel defining a path from said exterior surface of said body to said interior surface of said body, said path configured to direct exhaust gas flow to said soot sensor.

16. The system of claim 9, wherein said circuitry is configured activate said first element to operate in said second mode when said soot accumulated on said first element reaches a predetermined threshold level, said first element configured to heat to a temperature which removes at least a portion of said soot accumulated on said first element and said first surface of said substrate.

17. A method of measuring an amount of soot deposited on a soot sensor, said method comprising:
   obtaining a soot sensor comprising:
      a substrate defining a first surface and a second surface opposing said first surface;
      a first element having at least one continuous loop of conductive material disposed on said first surface of said substrate, said first element being configured to operate in a first mode to sense accumulation of soot on said first surface of said substrate and to operate in a second mode to remove accumulated soot on said first surface of said substrate; and
      a second element having at least one continuous loop of conductive material disposed on said first surface of said substrate, said second element being configured to operate in a first mode to sense accumulation of soot on said first surface of said substrate and to operate in a second mode to remove accumulated soot on said first surface of said substrate;
   monitoring a sense current through at least one of said first element or said second element, said current being representative of an amount of soot accumulated on said first element or said second element;
   providing heater current through at least one said first element or said second element in response to said monitoring step when said sense current reaches a predetermined threshold to thereby remove at least a portion of said soot accumulated on at least one of said first element or said second element; and
   detecting an open circuit of at least one of said first or said second elements based on a diagnostic sense current applied to said first or said second element.

* * * * *